(12) United States Patent
Spano, Jr. et al.

(10) Patent No.: US 8,170,714 B2
(45) Date of Patent: *May 1, 2012

(54) INTEGRATED SUITE OF MEDICAL TOOLS

(75) Inventors: Philip H. Spano, Jr., McKees Rocks, PA (US); Eric J. Switalski, Pittsburgh, PA (US)

(73) Assignee: McKesson Automation, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/958,065

(22) Filed: Dec. 1, 2010

(65) Prior Publication Data

US 2011/0071667 A1 Mar. 24, 2011

Related U.S. Application Data

(63) Continuation of application No. 10/996,835, filed on Nov. 24, 2004, now Pat. No. 7,865,263.

(60) Provisional application No. 60/525,396, filed on Nov. 26, 2003.

(51) Int. Cl.
*G06F 17/00* (2006.01)

(52) U.S. Cl. ......... 700/237; 700/232; 700/233; 700/241

(58) Field of Classification Search .................. 700/233, 700/232, 237, 241
See application file for complete search history.

(56) References Cited

U.S. PATENT DOCUMENTS

| | | | |
|---|---|---|---|
| 2,964,370 A | 12/1960 | Butler | |
| 3,556,342 A | 1/1971 | Guarr | |
| 3,593,881 A | 7/1971 | Paap | |
| 3,599,152 A | 8/1971 | Williams | |
| 3,606,959 A | 9/1971 | Stonor | |
| 3,675,816 A | 7/1972 | Bourke, II et al. | |
| 3,732,544 A | 5/1973 | Obland | |
| 3,744,867 A | 7/1973 | Shaw | |
| 3,762,601 A | 10/1973 | McLaughlin | |
| 3,858,181 A | 12/1974 | Goldsby et al. | |
| 3,875,982 A | 4/1975 | Mizu et al. | |
| 3,878,967 A | 4/1975 | Joslin et al. | |
| 3,917,045 A | 11/1975 | Williams et al. | |
| 3,948,454 A | 4/1976 | Bastian | |
| 3,998,356 A | 12/1976 | Christensen | |
| 4,020,972 A | 5/1977 | Lundblad | |
| 4,135,241 A | 1/1979 | Stanis et al. | |
| 4,225,930 A | 9/1980 | Steffen | |
| 4,237,536 A | 12/1980 | Enelow et al. | |
| 4,267,942 A | 5/1981 | Wick, Jr. et al. | |
| 4,293,845 A | 10/1981 | Villa-Real | |

(Continued)

FOREIGN PATENT DOCUMENTS

CA 936501 11/1973

(Continued)

*Primary Examiner* — Michael K Collins
(74) *Attorney, Agent, or Firm* — Alston & Bird LLP

(57) ABSTRACT

The present disclosure is directed to a tool that can be used to order, dispense, locate, request and administer medications as well as locate, issue and administer medical items and supplies for patients from a plurality of entry points into the system, e.g. handheld devices, mobile cart, etc. New workflows and functionality for various devices such as dispensing devices (automated dispensing cabinets) and issuing devices (e.g. open shelving) are also disclosed. Because of the rules governing abstracts, this abstract should not be used to construe the claims.

20 Claims, 21 Drawing Sheets

U.S. PATENT DOCUMENTS

| | | | |
|---|---|---|---|
| 4,342,404 A | 8/1982 | Baker | |
| 4,360,125 A | 11/1982 | Martindale et al. | |
| 4,412,292 A | 10/1983 | Sedam et al. | |
| 4,473,884 A | 9/1984 | Behl | |
| 4,504,153 A | 3/1985 | Schollmeyer et al. | |
| 4,546,901 A | 10/1985 | Buttarazzi | |
| 4,616,316 A | 10/1986 | Hanpeter et al. | |
| 4,655,026 A | 4/1987 | Wigoda | |
| 4,664,289 A | 5/1987 | Shimizu et al. | |
| 4,695,954 A | 9/1987 | Rose et al. | |
| 4,717,042 A | 1/1988 | McLaughlin | |
| 4,725,997 A | 2/1988 | Urquhart et al. | |
| 4,733,362 A | 3/1988 | Haraguchi | |
| 4,737,910 A | 4/1988 | Kimbrow | |
| 4,766,542 A | 8/1988 | Pilarczyk | |
| 4,766,548 A | 8/1988 | Cedrone et al. | |
| 4,779,938 A | 10/1988 | Johnston | |
| 4,785,969 A | 11/1988 | McLaughlin | |
| 4,811,764 A | 3/1989 | McLaughlin | |
| 4,812,629 A | 3/1989 | O'Neil et al. | |
| 4,813,752 A | 3/1989 | Schindler | |
| 4,813,753 A | 3/1989 | Relyea | |
| 4,831,562 A | 5/1989 | McIntosh et al. | |
| 4,839,806 A | 6/1989 | Goldfischer et al. | |
| 4,847,764 A | 7/1989 | Halvorson | |
| 4,857,713 A | 8/1989 | Brown | |
| 4,953,745 A | 9/1990 | Rowlett, Jr. | |
| 4,967,928 A | 11/1990 | Carter | |
| 5,014,875 A | 5/1991 | McLaughlin et al. | |
| 5,047,948 A | 9/1991 | Turner | |
| 5,171,120 A | 12/1992 | Bernard, II et al. | |
| 5,190,185 A | 3/1993 | Blechl | |
| 5,205,436 A | 4/1993 | Savage | |
| 5,246,332 A | 9/1993 | Bernard, II et al. | |
| 5,272,321 A | 12/1993 | Otsuka et al. | |
| 5,314,243 A | 5/1994 | McDonald et al. | |
| 5,346,297 A | 9/1994 | Colson, Jr. et al. | |
| 5,363,310 A | 11/1994 | Haj-Ali-Ahmadi et al. | |
| 5,377,864 A | 1/1995 | Blechl et al. | |
| 5,405,048 A | 4/1995 | Rogers et al. | |
| 5,408,443 A | 4/1995 | Weinberger | |
| 5,431,299 A | 7/1995 | Brewer et al. | |
| 5,438,523 A | 8/1995 | Humm et al. | |
| 5,460,294 A | 10/1995 | Williams | |
| 5,468,110 A | 11/1995 | McDonald et al. | |
| 5,472,309 A | 12/1995 | Bernard, II et al. | |
| 5,480,062 A | 1/1996 | Rogers et al. | |
| 5,484,991 A | 1/1996 | Sherman et al. | |
| 5,502,944 A | 4/1996 | Kraft et al. | |
| 5,520,450 A | 5/1996 | Colson, Jr. et al. | |
| 5,564,803 A | 10/1996 | McDonald et al. | |
| 5,585,473 A | 12/1996 | Bendiak | |
| 5,593,267 A | 1/1997 | McDonald et al. | |
| 5,597,995 A | 1/1997 | Williams et al. | |
| 5,608,643 A | 3/1997 | Wichter et al. | |
| 5,611,051 A | 3/1997 | Pirelli | |
| 5,661,978 A | 9/1997 | Holmes et al. | |
| D384,578 S | 10/1997 | Wangu et al. | |
| 5,713,485 A | 2/1998 | Liff et al. | |
| 5,716,114 A | 2/1998 | Holmes et al. | |
| 5,722,332 A | 3/1998 | Fumanelli | |
| 5,745,366 A | 4/1998 | Higham et al. | |
| 5,761,877 A | 6/1998 | Quandt | |
| 5,781,442 A | 7/1998 | Engleson et al. | |
| 5,790,409 A | 8/1998 | Fedor et al. | |
| 5,797,515 A | 8/1998 | Liff et al. | |
| 5,805,455 A | 9/1998 | Lipps | |
| 5,805,456 A | 9/1998 | Higham et al. | |
| 5,808,289 A | 9/1998 | Becker | |
| 5,820,237 A | 10/1998 | Robey | |
| 5,842,976 A | 12/1998 | Williamson | |
| 5,877,962 A | 3/1999 | Radcliffe | |
| 5,878,885 A | 3/1999 | Wangu et al. | |
| 5,880,443 A | 3/1999 | McDonald et al. | |
| 5,883,806 A | 3/1999 | Meador et al. | |
| 5,893,697 A | 4/1999 | Zini et al. | |
| 5,905,653 A | 5/1999 | Higham et al. | |
| 5,907,493 A | 5/1999 | Boyer | |
| 5,912,818 A | 6/1999 | McGrady et al. | |
| 5,927,540 A | 7/1999 | Godlewski | |
| 5,940,306 A | 8/1999 | Gardner et al. | |
| 5,957,372 A | 9/1999 | Dean et al. | |
| 5,971,593 A | 10/1999 | McGrady | |
| 5,993,046 A | 11/1999 | McGrady et al. | |
| 6,003,006 A | 12/1999 | Colella et al. | |
| 6,011,999 A | 1/2000 | Holmes | |
| 6,019,249 A | 2/2000 | Michael et al. | |
| 6,021,392 A | 2/2000 | Lester et al. | |
| 6,027,019 A | 2/2000 | Kou | |
| 6,039,467 A | 3/2000 | Holmes | |
| 6,065,819 A | 5/2000 | Holmes et al. | |
| 6,068,156 A | 5/2000 | Liff et al. | |
| 6,073,834 A | 6/2000 | Michael et al. | |
| 6,108,588 A | 8/2000 | McGrady | |
| 6,109,774 A | 8/2000 | Holmes et al. | |
| 6,112,502 A | 9/2000 | Frederick et al. | |
| 6,116,461 A | 9/2000 | Broadfield et al. | |
| 6,151,536 A | 11/2000 | Arnold et al. | |
| 6,152,364 A * | 11/2000 | Schoonen et al. | 235/375 |
| 6,170,230 B1 | 1/2001 | Chudy et al. | |
| 6,170,929 B1 | 1/2001 | Wilson | |
| 6,175,779 B1 | 1/2001 | Barrett | |
| 6,176,392 B1 | 1/2001 | William et al. | |
| 6,181,982 B1 | 1/2001 | Yuyama et al. | |
| 6,189,727 B1 | 2/2001 | Shoenfeld | |
| 6,189,788 B1 | 2/2001 | Sherman et al. | |
| 6,223,934 B1 | 5/2001 | Shoenfeld | |
| 6,256,967 B1 | 7/2001 | Hebron et al. | |
| 6,283,322 B1 | 9/2001 | Liff et al. | |
| 6,289,656 B1 | 9/2001 | Wangu et al. | |
| 6,317,648 B1 | 11/2001 | Sleep et al. | |
| 6,332,100 B1 | 12/2001 | Sahai et al. | |
| 6,338,007 B1 | 1/2002 | Broadfield et al. | |
| 6,339,732 B1 | 1/2002 | Phoon et al. | |
| 6,354,783 B1 | 3/2002 | Stoy et al. | |
| 6,361,263 B1 | 3/2002 | Dewey et al. | |
| 6,364,517 B1 | 4/2002 | Yuyama et al. | |
| 6,370,841 B1 | 4/2002 | Chudy et al. | |
| 6,385,505 B1 | 5/2002 | Lipps | |
| 6,393,339 B1 | 5/2002 | Yeadon | |
| 6,418,416 B1 | 7/2002 | Rosenberg et al. | |
| RE37,829 E | 9/2002 | Charhut et al. | |
| 6,449,927 B2 | 9/2002 | Hebron et al. | |
| 6,470,234 B1 | 10/2002 | McGrady | |
| 6,471,089 B2 | 10/2002 | Liff et al. | |
| 6,490,502 B2 | 12/2002 | Fellows et al. | |
| 6,497,342 B2 | 12/2002 | Zhang et al. | |
| 6,499,270 B2 | 12/2002 | Peroni et al. | |
| 6,529,801 B1 | 3/2003 | Rosenblum | |
| 6,530,517 B1 | 3/2003 | Kou | |
| 6,532,399 B2 | 3/2003 | Mase | |
| 6,564,121 B1 | 5/2003 | Wallace et al. | |
| 6,581,798 B2 | 6/2003 | Liff et al. | |
| 6,604,019 B2 | 8/2003 | Ahlin et al. | |
| 6,609,047 B1 | 8/2003 | Lipps | |
| 6,611,733 B1 | 8/2003 | De La Huerga | |
| 6,625,952 B1 | 9/2003 | Chudy et al. | |
| 6,636,780 B1 | 10/2003 | Haitin et al. | |
| 6,640,159 B2 | 10/2003 | Holmes et al. | |
| 6,650,964 B2 * | 11/2003 | Spano et al. | 700/237 |
| 6,671,579 B2 | 12/2003 | Spano, Jr. et al. | |
| 6,681,149 B2 | 1/2004 | William et al. | |
| 6,733,095 B1 | 5/2004 | Rieb | |
| 6,735,497 B2 | 5/2004 | Wallace et al. | |
| 6,742,671 B2 | 6/2004 | Hebron et al. | |
| 6,755,931 B2 | 6/2004 | Vollm et al. | |
| 6,760,643 B2 | 7/2004 | Lipps | |
| 6,775,591 B1 | 8/2004 | Shoenfeld | |
| 6,776,304 B2 | 8/2004 | Liff et al. | |
| 6,785,589 B2 | 8/2004 | Eggenberger et al. | |
| 6,788,997 B1 | 9/2004 | Frederick | |
| 6,790,198 B1 | 9/2004 | White et al. | |
| 6,811,088 B2 | 11/2004 | Lanzaro et al. | |
| 6,814,254 B2 | 11/2004 | Liff et al. | |
| 6,814,255 B2 | 11/2004 | Liff et al. | |
| 6,823,084 B2 | 11/2004 | Myers et al. | |
| 6,847,861 B2 | 1/2005 | Lunak et al. | |

| | | |
|---|---|---|
| 6,871,783 B2 * | 3/2005 | Kaafarani et al. .............. 235/380 |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,935,560 B2 | 8/2005 | Andreasson et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 | 5/2006 | Broadfield et al. |
| 7,052,097 B2 | 5/2006 | Meek, Jr. et al. |
| 7,072,737 B2 | 7/2006 | Lunak et al. |
| 7,072,840 B1 * | 7/2006 | Mayaud ............................ 705/2 |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,155,306 B2 | 12/2006 | Haitin et al. |
| 7,171,277 B2 | 1/2007 | Engleson et al. |
| 7,218,231 B2 | 5/2007 | Higham |
| 7,228,198 B2 | 6/2007 | Vollm et al. |
| 7,249,688 B2 | 7/2007 | Hunter et al. |
| 7,260,402 B1 | 8/2007 | Ahmed |
| 7,348,884 B2 | 3/2008 | Higham |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,554,449 B2 | 6/2009 | Higham |
| 7,568,827 B2 | 8/2009 | Lee et al. |
| 7,571,024 B2 | 8/2009 | Duncan et al. |
| 7,588,167 B2 | 9/2009 | Hunter et al. |
| 7,865,263 B2 * | 1/2011 | Spano et al. .................. 700/237 |
| 2001/0032035 A1 | 10/2001 | Holmes et al. |
| 2002/0032582 A1 | 3/2002 | Feeney, Jr. et al. |
| 2002/0091593 A1 | 7/2002 | Fowler |
| 2002/0095238 A1 | 7/2002 | Ahlin et al. |
| 2002/0147597 A1 | 10/2002 | Connors et al. |
| 2003/0060926 A1 | 3/2003 | Yuyama et al. |
| 2003/0105555 A1 | 6/2003 | Lunak et al. |
| 2003/0117281 A1 | 6/2003 | Sriharto et al. |
| 2003/0120384 A1 | 6/2003 | Haitin et al. |
| 2003/0144882 A1 | 7/2003 | Talachian et al. |
| 2003/0195654 A1 * | 10/2003 | Spano et al. .................. 700/237 |
| 2004/0054436 A1 | 3/2004 | Haitin et al. |
| 2004/0104652 A1 | 6/2004 | Holmes et al. |
| 2004/0225527 A1 | 11/2004 | Holz |
| 2004/0225528 A1 | 11/2004 | Brock |
| 2005/0096785 A1 | 5/2005 | Moncrief et al. |
| 2005/0113970 A1 | 5/2005 | Holmes et al. |
| 2005/0149379 A1 | 7/2005 | Cyr et al. |
| 2005/0216310 A1 | 9/2005 | Clements et al. |
| 2006/0079994 A1 | 4/2006 | Chu et al. |
| 2006/0190297 A1 | 8/2006 | Glass et al. |

FOREIGN PATENT DOCUMENTS

| | | |
|---|---|---|
| CA | 2412801 | 5/2003 |
| DE | 3040580 | 5/1982 |
| DE | 3205620 | 9/1982 |
| EP | 0037649 A2 | 10/1981 |
| EP | 0208029 A1 | 1/1987 |
| EP | 0249367 A2 | 12/1987 |
| JP | 77051755 | 12/1978 |
| JP | 78058513 | 11/1979 |
| JP | 83076764 | 5/1983 |
| JP | 84056958 | 4/1984 |
| JP | 8345388 | 10/1984 |
| JP | 85069771 | 10/1986 |
| JP | 85112661 | 12/1986 |
| WO | WO 86/06048 | 10/1986 |
| WO | WO 03/071943 | 9/2003 |
| WO | WO 2006/078737 A2 | 7/2006 |

* cited by examiner

- Patient's Cassette = Dispensed by Robot, MedCarousel or MedShelf in Pharmacy

- Each AcuDose-Rx cabinet in the nursing unit is listed showing which of the patient"s meds they have

- Unknown drugs are those not in any AcuDose-Rx cabinet in the unit or in a cassette

| 1 AdminRx | Nurse 1 |
|---|---|
| Dispense List ||
| A \| Test 1000, Pat | \| 1AR 100 01 |
| Patient's Cassette ||
| ⬇ Drug 1  10mg SCHD ||
| 1AR's Cabinet Station: 1 ||
| ✓all | |
| ☐ Drug 2  20mg SCHD ||
| ☐ Drug 3  30mg NOW ||
| ☐ Drug 4  40mg SCHD ||
| ℞ Unkown ||
| ℞ Drug 5  50mg ONCE ||
| ℞ Drug 6  60mg SCHD ||
| OK | Cancel | Add |

*Fig.4C*

| 1 AdminRx | Nurse 1 |
|---|---|
| Active Non-Due List ||
| A \| Test 1000, Pat | \| 1AR 100 01 |
| ☐ Drug 7  325mg PRN ||
| ☐ Drug 8  10mg PRN ||
| ☐ Drug 9  100mg SCHD ||
| ☐ Drug 10  40mg PRN ||
| OK | Cancel |

*Fig.4D*

| 1 AdminRx | Nurse 1 |
|---|---|

Dispense List

| A | Test 1000, Pat | 1AR 100 01 |
|---|---|---|
| ⬇ | Patient's Cassette | |
| ⬇ | Drug 1  10mg SCHD | |
| ⬇ | Drug 7  325mg PRN | |
| ⬇ | Drug 10  40mg PRN | |
| ✓all | 1AR's Cabinet Station: 1 | |
| ☐ | Drug 2  20mg SCHD | |
| ☐ | Drug 3  30mg NOW | |
| ☐ | Drug 4  40mg SCHD | |
| ☐ | Drug 9  100mg SCHD | |
| ℞ | Unkown | |
| ℞ | Drug 5  50mg ONCE | |
| ℞ | Drug 6  60mg SCHD | |
| ℞ | Drug 8  10mg PRN | |

| OK | Cancel | Add |
|---|---|---|

*Fig.4E*

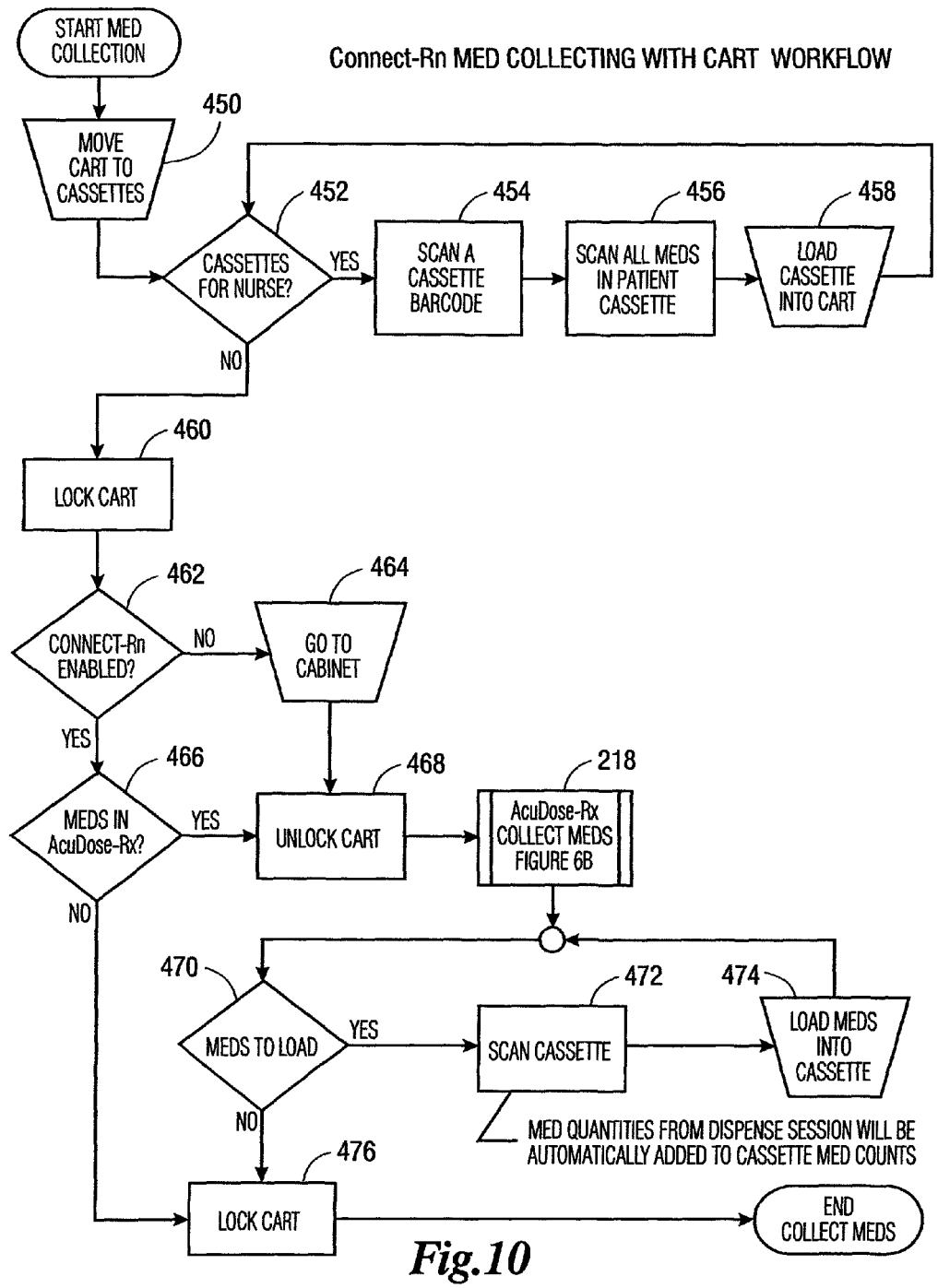

INTEGRATED SUITE OF MEDICAL TOOLS

The present invention is a continuation application of U.S. application Ser. No. 10/996,835, filed on Nov. 24, 2004 now U.S. Pat. No. 7,865,263, which claims priority from U.S. application Ser. No. 60/525,396 filed Nov. 26, 2003, and entitled Integrated Suite of Medical Tools, each of which is hereby incorporated by reference in its entirety.

BACKGROUND OF THE INVENTION

The present disclosure is related to computer operated devices for controlling the ordering, dispensing, issuing and administration of medical items including drugs and supplies for patients.

There currently exists a number of devices that may be used in a healthcare setting for controlling the ordering, dispensing, and administration of medical items, including drugs and supplies, under the control of a computer. Performing such functions under the control of a computer allows data to be gathered that can be used for billing, reordering of stock as well as creating an audit trail. Such devices include, for example, imaging devices for inputting new prescriptions or new orders for patients into a central pharmacy system, computer controlled dispensing cabinets, hand held scanners that can be used for bedside administration of drugs, and open bins of supplies having a local computer into which information relating to the issuing of supplies for patients can be logged. Such devices can be purchased from a variety of vendors.

Some devices, such as the handheld bedside scanners, require a substantial investment in infrastructure which may create a bather in the sales process. In U.S. patent application Ser. No. 09/998,121 filed Nov. 30, 2001 and entitled Method Of Issuing Medical Supplies And Dispensing and Administering Medications Through A Hand-Held Device And System For Doing The Same, which is hereby incorporated by reference, the assignee of the present invention has proposed integrating into their handheld bedside scanner the ability to issue medical supplies from open bin storage shelving. However, the investment in such infrastructure is not currently being fully leveraged to provide advantages for other devices used by nurses such as the imaging devices and computer controlled cabinets.

From the user's point of view, integrating into one device the ability to dispense medications, issue supplies, and administer dispensed medications seems convenient, but the underlying infrastructure and rules applicable to each of these processes makes integration difficult. For example, medications are typically dispensed by a pharmacy. The pharmacy may be set up using a centralized dispensing model, decentralized dispensing model, or a combination of the two. In each of the three models, various combinations of automated (e.g. unit based dispensing cabinets), partially automated (e.g. carousels), or manual (e.g. open shelving) equipment may be used. As medications are dispensed, counts must be maintained to insure that the pharmacy does not run out of the needed medications. Counts may be maintained automatically in computer controlled devices, manually, or a combination of both. Provision must also be made to accommodate returned medications that have been dispensed for a patient but have not been administered, e.g. the patient has been discharged, prescription has been changed, etc.

The pharmacy must also be capable of interaction with other systems. For example, the pharmacy is responsible for communicating with insurance companies or clearing houses to determine if a patient's insurance allows for substitution and, if so, what are the allowable substitutes, as well as to determine what the patient's insurance will pay for. The pharmacy system must interface with the healthcare facility's billing system and systems for reordering medications.

As might be expected, the pharmacy is governed by various rules. For example, in all cases, except certain emergency situations, medications dispensed for a patient must be reviewed by a pharmacist. Rules may be in place that require each prescribed medication to be cross-checked for interactions with other medications ordered for the patient and to be checked against known patient allergies. The pharmacy may also be responsible for tracking the age and lot numbers of medications to insure that expired medications and recalled medications are quickly removed from the distribution chain. When one considers that a pharmacy must perform all these functions and follow all these rules for perhaps thousands or even tens of thousand of prescriptions a day, it is easy to understand that the operation of a pharmacy has become a complicated and specialized process.

In addition to dispensing drugs for administering to a patient, a nurse or other healthcare worker may also need to have supplies issued for a patient. Supplies are typically controlled by a materials management department within a healthcare facility. Supplies typically are not regulated as are medications and therefore materials management departments often do not need to follow the same strict rules that are applicable to pharmacies. Nevertheless, the materials management department must be able to keep track of current inventories to insure that all needed supplies are on hand. That can be a daunting task for several reasons. First, there may be thousands of items in inventory. For each item, that item may be available from various suppliers at different prices with each supplier using its own unique stock number. Also, supplies are often kept in open bins or shelving. When items are removed, it is up to the user to remember to document the items' removal. Often times, such documentation is not performed, and items can be low or out of stock without the materials management department learning of such situations until a manual count is performed. The materials management department must interact with the healthcare facility's billing system and supplier's systems for reordering supplies.

The nursing function is one way that the healthcare facility interacts with patients. Nurses dispense medications for patients, either from a centralized or decentralized pharmacy. Nurses also issue supplies for patients. It can be time consuming to dispense all the necessary medications and issue all the necessary supplies for each patient on the current round for that nurse as medications and supplies are not kept in the same storage locations, and both medications and supplies may not be where they are supposed to be located. Also the procedures for dispensing medications are different than the procedures for issuing supplies. For example, the procedure for dispensing a medication from a unit based cabinet is very different from the procedure for issuing a supply from open bins. Finally, the administering of medications to a patient is strictly governed by rules, whereas the delivery of supplies to a patient is not. The administration of medications must insure that the right patient, receives the right dose of the right drug, via the right route, at the right time. The administration process must also be documented to create an audit trial. Thus, in addition to tending to the needs of patients, a nurse must be aware of a variety of different dispensing and administering schemes for drugs as well as issuing and delivery schemes for supplies.

Nursing has identified certain problems in dispensing schemes utilizing computer controlled dispensing cabinets. One problem is nurses taking central pharmacy dispensed medications from a patient specific cassette for another patient that is assigned to another nurse. In such situations, medications cannot be found where they are expected to be. Another problem is that nurses waste time waiting in lines at computer controlled dispensing cabinets at peak times. It would save significant time if nurses could either get all their medications in one place or if they knew exactly where to go to get the medications they needed. Existing infrastructure could also be leveraged if additional functionality could be added to devices currently being used for other functions.

BRIEF SUMMARY OF THE INVENTION

The present disclosure is directed to an integrated suite of tools for controlling the ordering, dispensing, issuing and administration of medical items including drugs and supplies for patients from a plurality of entry points into the system, e.g. handheld devices, mobile cart, etc. New workflows and functionality for various devices such as dispensing devices (automated dispensing cabinets) and issuing devices (e.g. open shelving) are also disclosed.

One embodiment of the present disclosure is directed to a system having an automated medication dispensing device. A computer located remotely of the automated dispensing device communicates with the dispensing device, or a database that maintains an inventory of items located within the dispensing device, and sends a queue of dispensing orders to the dispensing device. An authentication device confirms when the user is located proximate to the dispensing device. The dispensing device is responsive to the authentication device for performing the queued dispensing orders.

Another embodiment of the present disclosure is directed to a system having a medication dispensing system and a computer located remotely of the dispensing system for communicating with the medication dispensing system, or a database that maintains an inventory of items located within the dispensing system, to identify a location within the medication dispensing system where items to be dispensed are located.

Another embodiment of the present disclosure is directed to a method comprising: inputting logon information into a system via a remote computer; creating via the remote computer a list of medications to dispense; verifying that an authorized user is located proximate to a dispensing device; transmitting the list of medications to the dispensing device; and dispensing the medications on the list.

Another embodiment of the present disclosure is directed to a method comprising: inputting logon information into a system via a remote computer; maintaining in a database an inventory of items located within a dispensing device; communicating with the database via the remote computer to build a list of medications to be dispensed; verifying that an authorized user is located proximate to the dispensing device; transmitting the list of medications to the dispensing device; and dispensing the medications on the list.

Another embodiment of the present disclosure is directed to a method comprising: inputting logon information into a system via a remote computer; and identifying via the remote computer a location within a medication dispensing system where items to be dispensed are located.

Another embodiment of the present disclosure is directed to a method comprising: inputting logon information into a system via a remote computer; maintaining in a database an inventory of items located within a dispensing system; and communicating with the database via the remote computer to identify a location within the medication dispensing system where a medication to be dispensed is located.

BRIEF DESCRIPTION OF THE DRAWINGS

For the present disclosure to be easily understood and readily practiced, the present disclosure will now be described, for purposes of illustration and not limitation, in conjunction with the following figures, wherein:

FIGS. 4C, 4D, and 4E are exemplary screen shots of information that can be illustrated at various points in the workflow of FIGS. 4A and 4B;

FIG. 10 illustrates an alternative workflow to the workflow illustrated in FIG. 6A in the event that a cart is available.

DETAILED DESCRIPTION OF THE INVENTION

Figure 1:
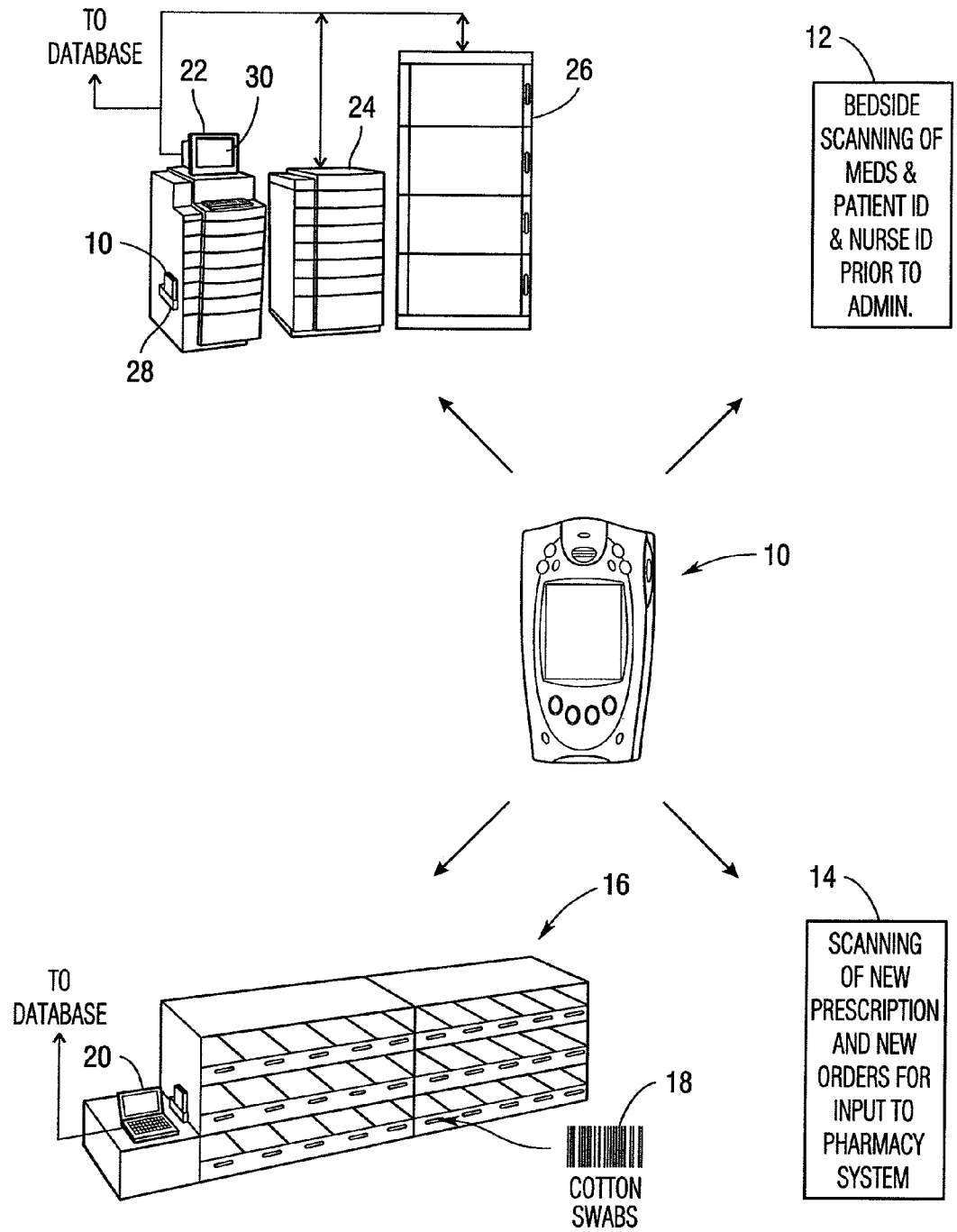
FIG. 1 is a diagram illustrating the use of a handheld device to control the operation of a variety of different devices.

FIG. 1 illustrates a handheld device 10. The handheld device 10 may be embodied in a variety of platforms including personal computers, tablet personal computers, PDA's, and the like. One type of handheld device 10 is a commercially available device such as the AdminRx handheld device available from McKesson Automation Inc. Such handheld devices are typically programmed to operate as wireless medication scanners used at the point of care to verify and chart medication administrations while providing a legible, real time medication administration record as shown by box 12. By scanning the medication, patient identification, and nurse identification, such handheld devices help to prevent life-threatening and costly medication errors by confirming the right patient, right medication, right dose, right time and right route.

Vendors of handheld device 10 now offer CCD barcode scanners that support imaging. That will allow a nurse to use a handheld device to scan an image of a doctor's written prescription, or new order for a patient, and submit it for input to the pharmacy system as illustrated by the box 14. The equipment represented by box 14 could also be, for example, a MedDirect product available from McKesson Automation Inc.

With appropriate programming of handheld device 10, a nurse could walk into a supply storage area with handheld device 10 and scan a barcode that identifies a particular storage location. For example, if open shelving 16 is provided, the nurse could scan a barcode, such as barcode 18. The nurse could then use the handheld to begin scanning supply products to be issued for a chosen patient. Multiple nurses could work in an open supply area at the same time. Also, supply areas would not necessarily need a nurse workstation any longer, such as workstation 20. If workstation 20 is eliminated, the replenishment function may be added to the handheld device 10. Although the supply storage area illustrated in FIG. 1 shows open shelving 16, other types of storage may be provided such as, for example, towers, whether locked or unlocked, carousels, and the like. If the supply storage area is locked, the user would use the handheld device 10 to unlock the storage device.

In the upper left hand corner of FIG. 1 a dispensing cabinet 22, auxiliary cabinet 24, and lockable tower 26 are illustrated. By providing nurses with functionality on the handheld device 10 to later control dispensing from a dispensing device, it is possible to guide them to either the patient cassette and/or cabinet/tower/etc. to find their medications the first time. As a result, nurses would be less likely to borrow medications from another patient's cassette if they are steered to where they are certain they can find the medication. Nurses could also use the handheld device 10 to request medications be sent up stat from a central pharmacy. Nurses could also significantly reduce their time in front of a cabinet by logging on to the handheld device 10, selecting one or more patients, and selecting the medications to be dispensed for each of the selected patients. Thereafter, when they step up to the dispensing cabinet 22, they can transfer the information about the selected patient and the medications to be dispensed to the cabinet by any suitable means. For example, the handheld device 10 may be docked in cradle 28 or the information may be wirelessly transferred to the cabinet 22. Thus, when the nurse has access to the cabinet, the nurse can immediately begin dispensing for patients instead of beginning the patient dispensing process by selecting patients and medications from touch screen 30.

The handheld device 10 could be replaced by a computer on a mobile cart (not shown). Other computers, located remotely of the dispensing devices such as shelving 16 and cabinet 24, may be used to provide certain of the functionality illustrated in FIG. 1. For example, a computer at a nursing station could be used to scan new prescriptions and provide the functionality of box 14 as well as construct a queue of dispensing orders to be transmitted to the cabinet 22. Clearly, if the remote computer is not mobile, it cannot be taken into a storage room where supplies are kept or to the patient's bedside. Thus, it is not necessary that all of the functions illustrated in FIG. 1 be present in any particular device or system.

By providing additional functionality, handheld devices 10 could become personal devices, assigned to and registered to a caregiver at the start of a shift. Alerts, messaging, and voice communications could then be added to the device.

Various dataflows and workflows will now be described for purposes of illustrating the disclosure. The concepts disclosed herein are not to be limited to the illustrated dataflows and workflows.

Figure 2:
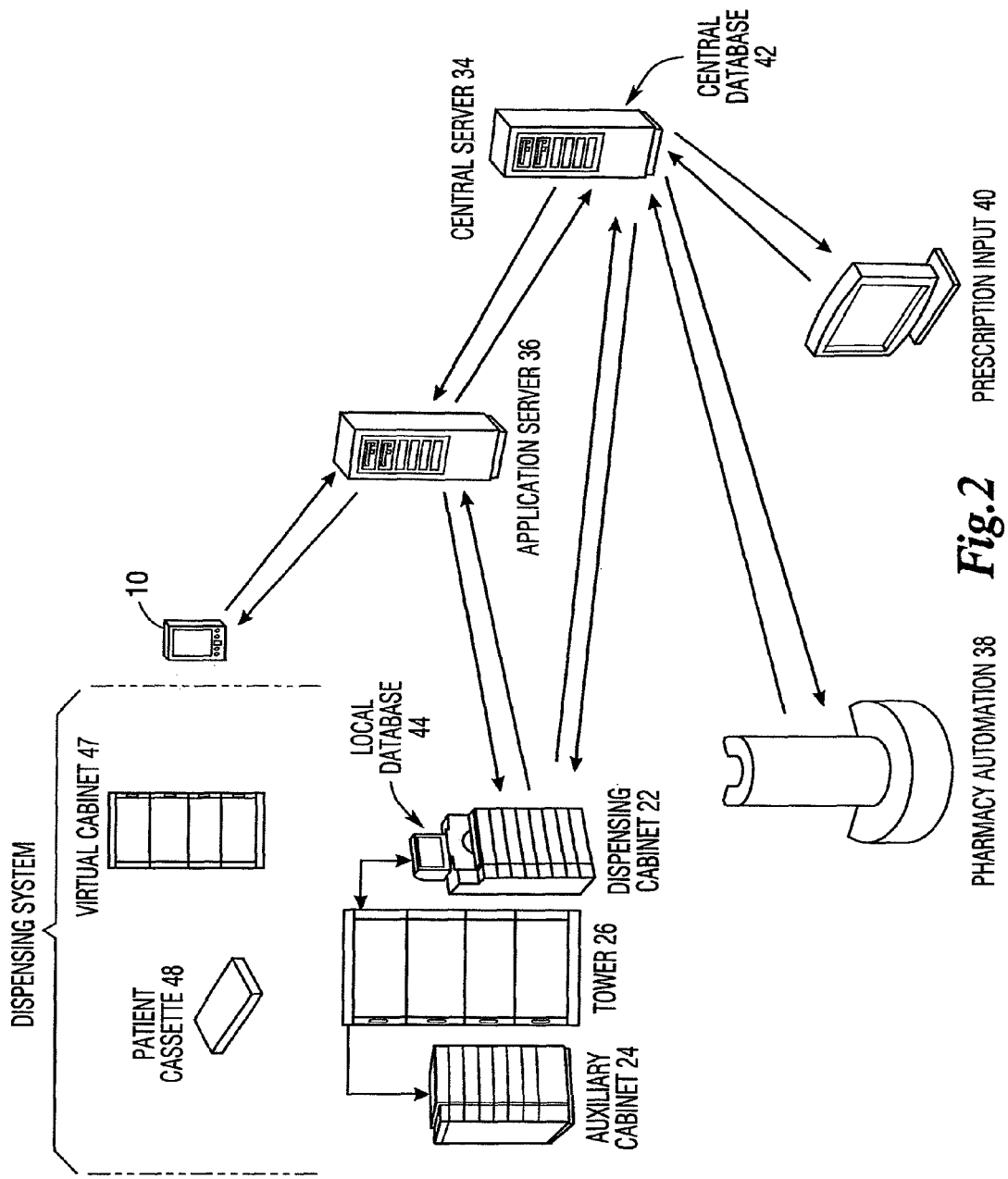
FIG. 2 illustrates a flow of data between a handheld device, an application server, a central server, a distributed dispensing cabinet, pharmacy automation, and prescription input devices.

Turning now to FIG. 2, a flow of data for one particular architecture is shown for purposes of illustration and not limitation. Data flows between the handheld device 10 and a central server 34 through an application server 36. The handheld device 10 may obtain order status from the central server 34. The handheld device 10 may create override orders or send missing medication requests to the central server 34. A central database 42 may reside on the central server 34. The central database 42 may be a Connect-Rx database available from McKesson Automation Systems, Inc., although other database products may be used. The location of the central database 42 will depend upon the functionality to be provided by the various components such that the location of the central database 42 is not important in the context of the present invention.

In FIG. 2, communication between the handheld device 10 and the dispensing cabinet 22 through the application server 36 is also illustrated. Resident on the dispensing cabinet 22 or associated therewith, is a local database 44. Data in the form of a list of medications to be dispensed is sent to the local database 44 and information regarding the availability of the medications is sent from the database 44 to the handheld device 10. A login procedure may also be executed between the handheld device 10 and the cabinet 22. The dispensing cabinet 22 is also capable of creating override orders which are input to the local database 44. The dispensing cabinet 22 is just one component of a dispensing system which may include, for example, auxiliary cabinet 24, tower 26, a virtual cabinet 47, a patient cassette 48, open shelving (not shown in FIG. 2), a medication storage room (not shown), among others.

A replication function 46 may provide override orders from the local database 44 to the central database 42, as well as to insure that the information on the two databases is consistent.

Missing medication requests may be sent to automation equipment 38 such as the McKesson Robot-Rx automation device and the McKesson MedCarousel automation device from the central database 42.

The central database 42 is also in communication with a McKesson MedDirect order entry system 40 or other prescription input device and a printer (not shown) to create medication orders, missing medication notifications and override order notifications. The reader should understand that the dataflow illustrated in FIG. 2 is exemplary only and that other dataflows may be implemented depending upon the capabilities of the various equipment comprising the system.

Figure 3:
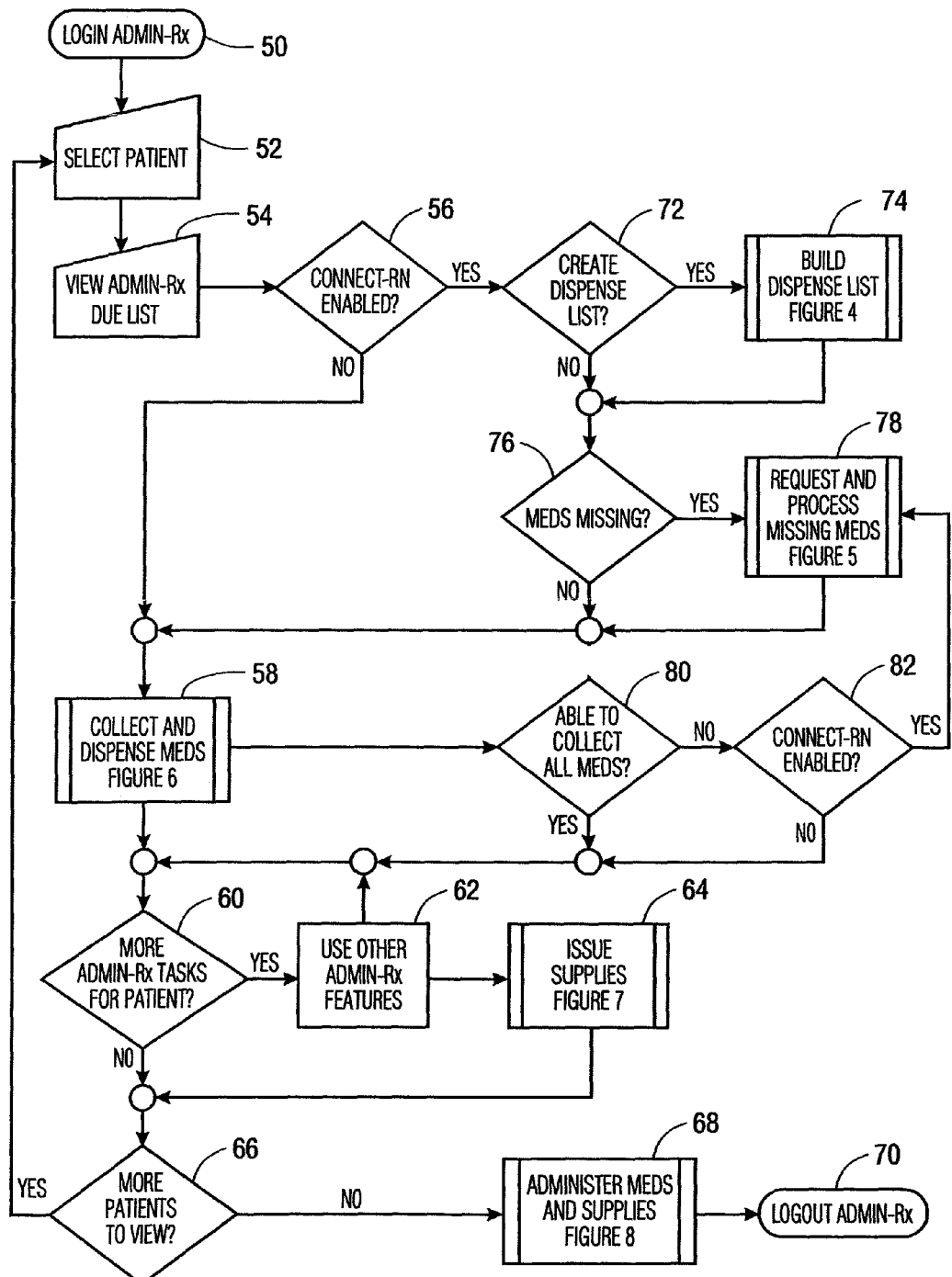
FIG. 3 is an overview of an exemplary workflow embodying the principles of the instant disclosure.

FIG. 3 is an overview of an exemplary workflow embodying the principles of the instant disclosure. In FIG. 3, a login procedure is carried out at 50. The login procedure may be the normal login procedure used on a remote computer such as the Admin-Rx device. Thereafter, at 52, the user may select a patient through any convenient manner, i.e., pick list, manually entered, scanning a bar code, etc. The user may then view the patient's ordered medications and may choose those medications to be dispensed so that they may be later administered to the patient.

After the patient is selected at 52, a due list is viewed at 54. The due list indicates all of the medications which that healthcare worker is to administer in the next medical administration round (MAR). Thereafter, an inquiry 56 determines whether Connect-Rn is enabled. Connect-Rn refers to a software module that embodies the principles of the present invention. It is anticipated that in facilities currently using the Admin-Rx device 10 as well as McKesson dispensing cabinets 22, that Connect-Rn will be a software module that can be purchased to enable the data flows discussed above in conjunction with FIG. 2. If Connect-Rn is not enabled, then process flow continues with a process 58. Process 58 represents the collect and dispense medication process which is described in greater detail in FIGS. 6A-6F. After the medications have been collected and dispensed through process 58, an inquiry 60 determines if there are more Admin-Rx tasks for this patient. If the answer is yes, then other features available on the Admin-Rx device are used at 62. For example, a process 64 may be carried out in which supplies may be issued in accordance with the work flow illustrated in FIG. 7. After the other features have been used, or if there are no more Admin-Rx tasks for this patient, an inquiry 66 is made as to whether there are more patients to view. If that determination is affirmative, process flow returns to 52. If there are no more patients to view, then the healthcare worker may proceed to administer the medications and supplies according to the workflow illustrated in FIG. 8, represented by box 68 in FIG. 3. Thereafter, the healthcare worker may logout at 70.

Figure 4A:
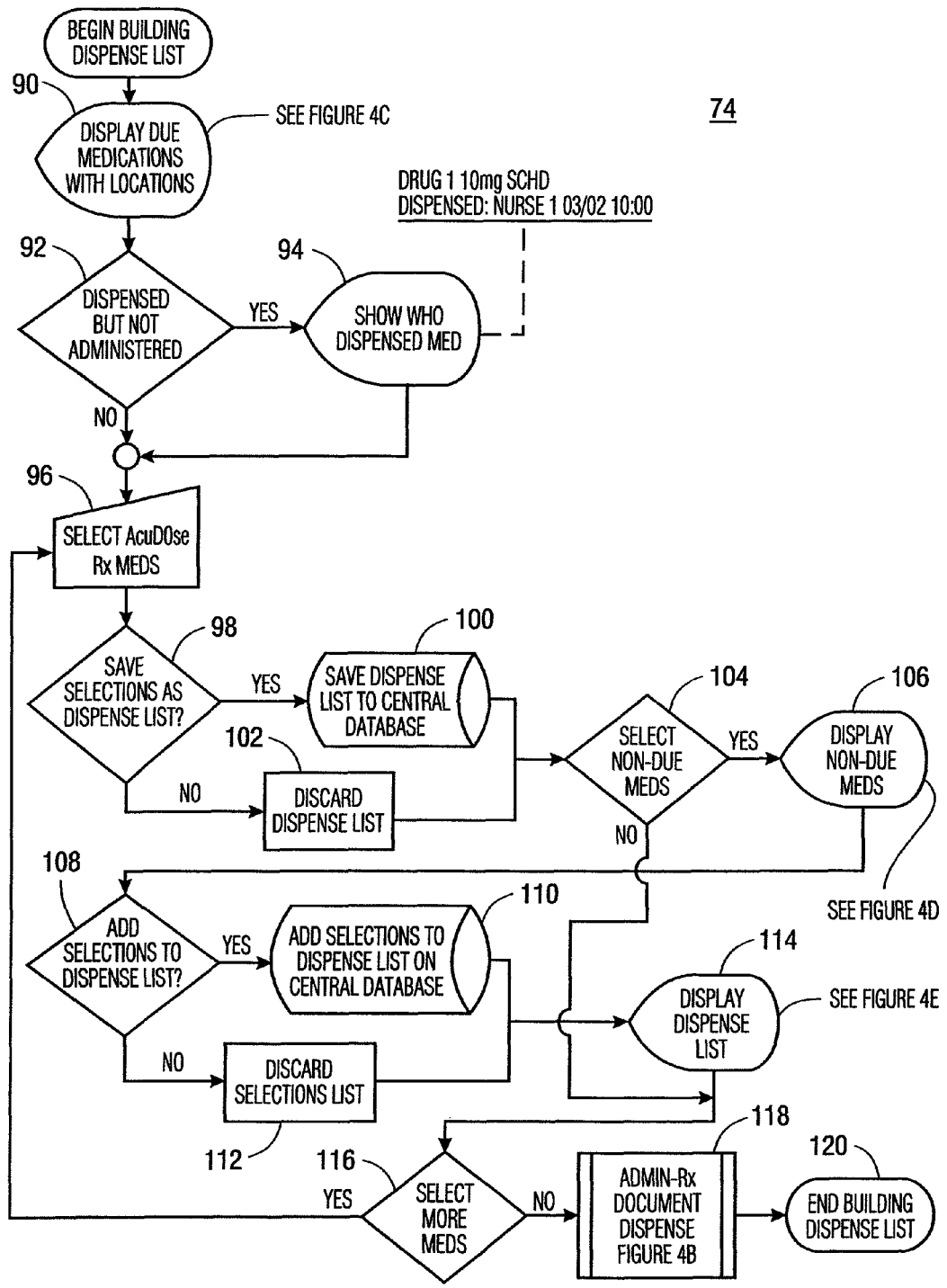
FIGS. 4A and 4B illustrate a workflow for building a list of medications to dispense and a document dispense workflow, respectively.
Figure 4B:
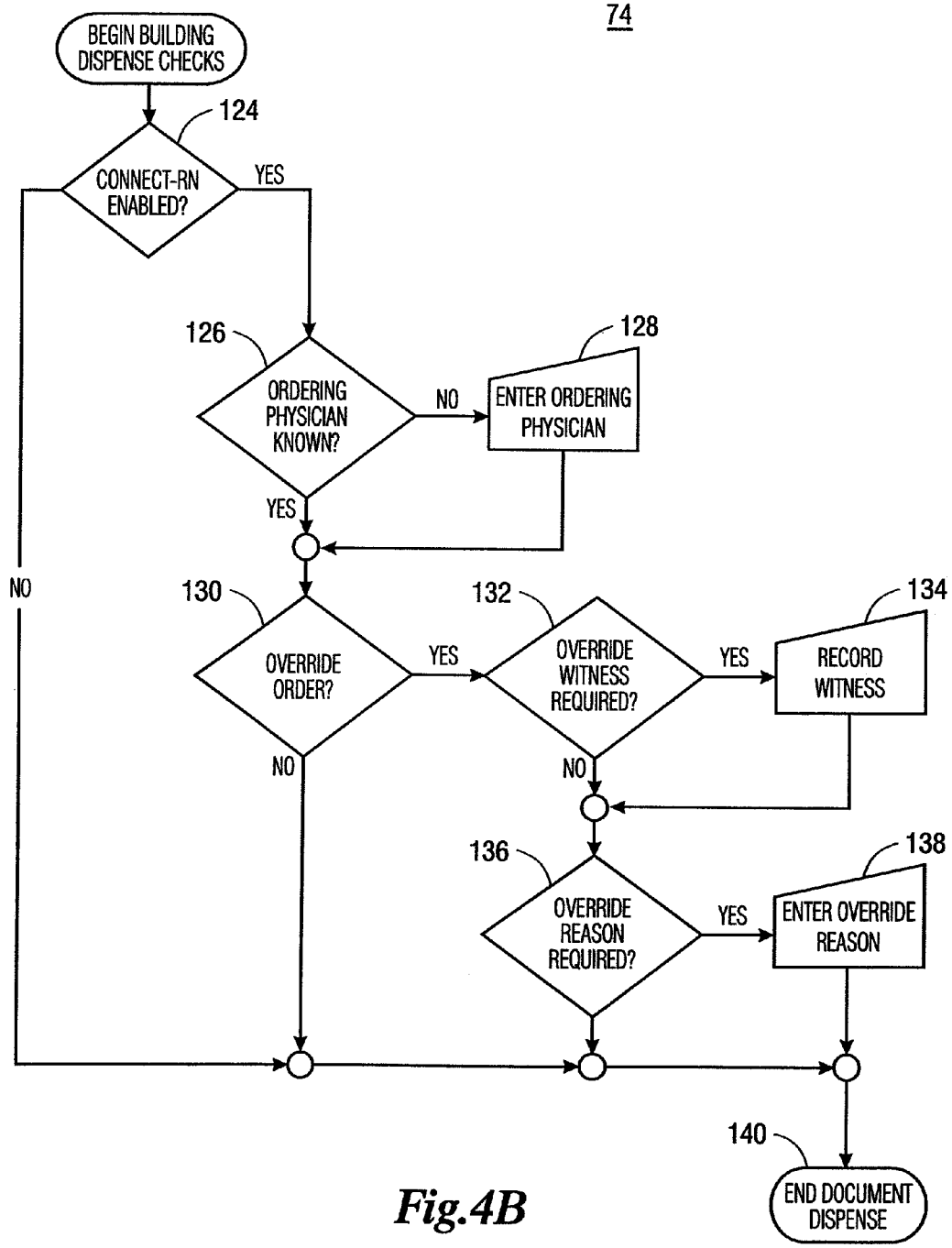
Figure 5A:
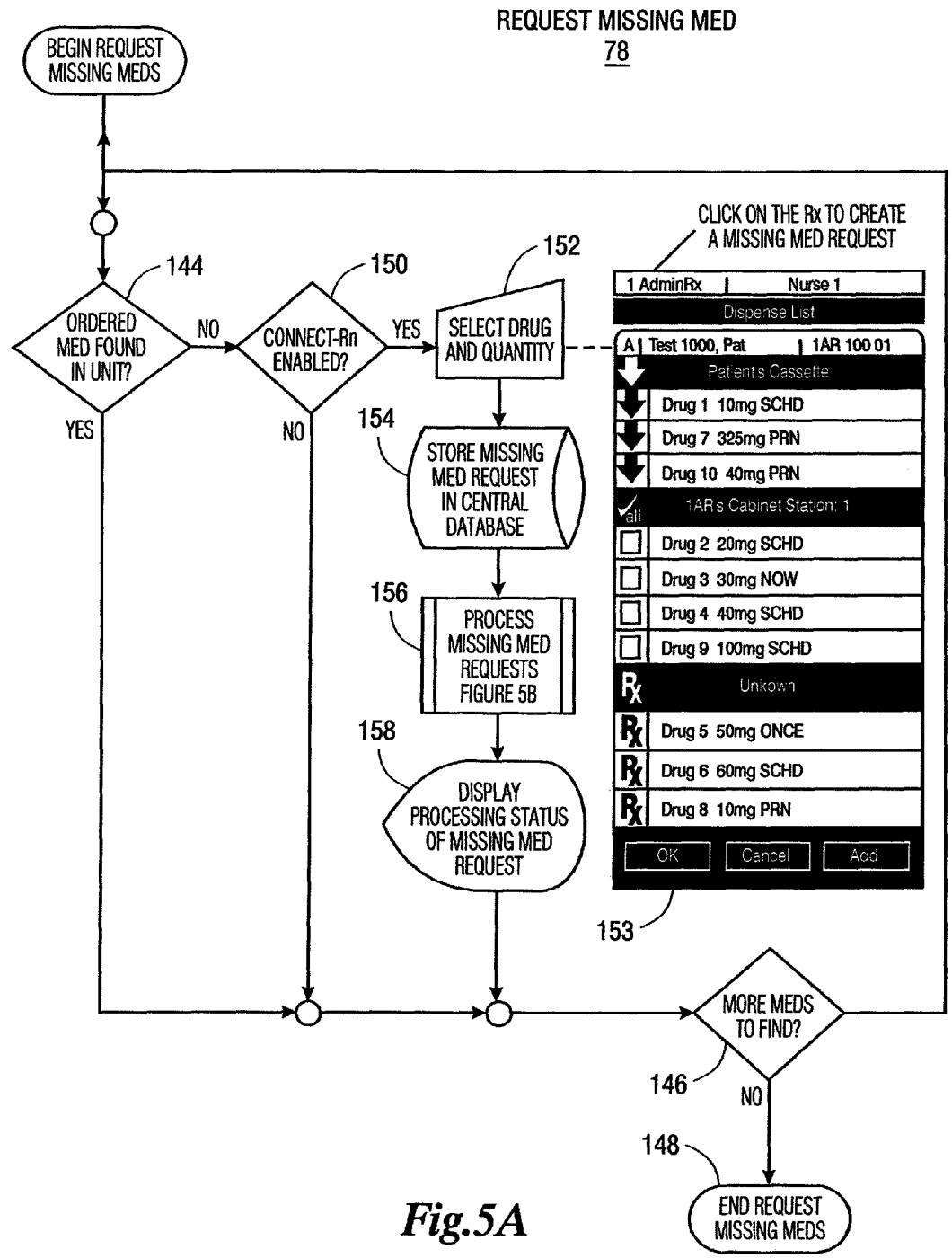
FIGS. 5A, 5B and 5C illustrate a workflow for generating and handling requests for missing medications.
Figure 5B:
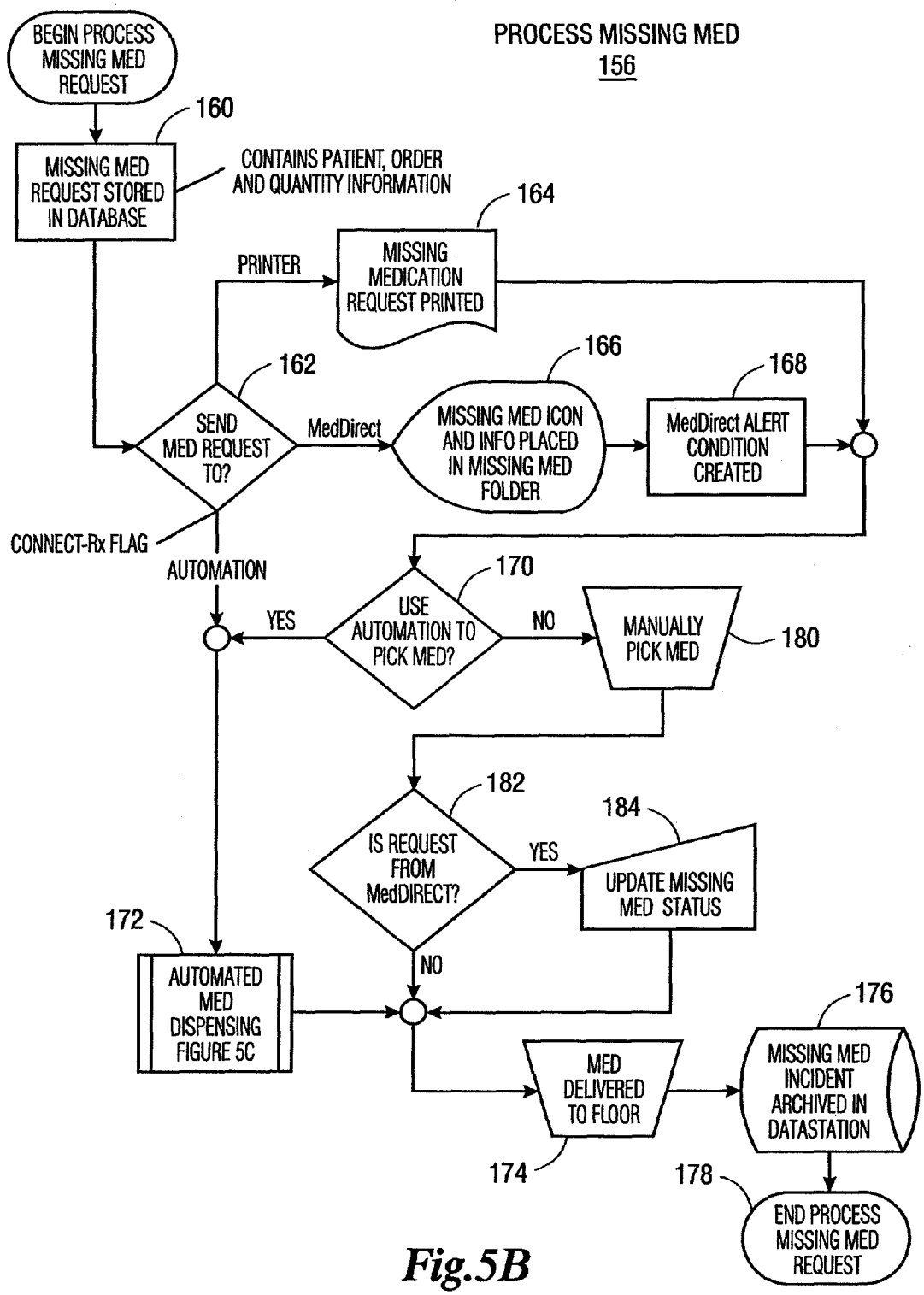
Figure 5C:
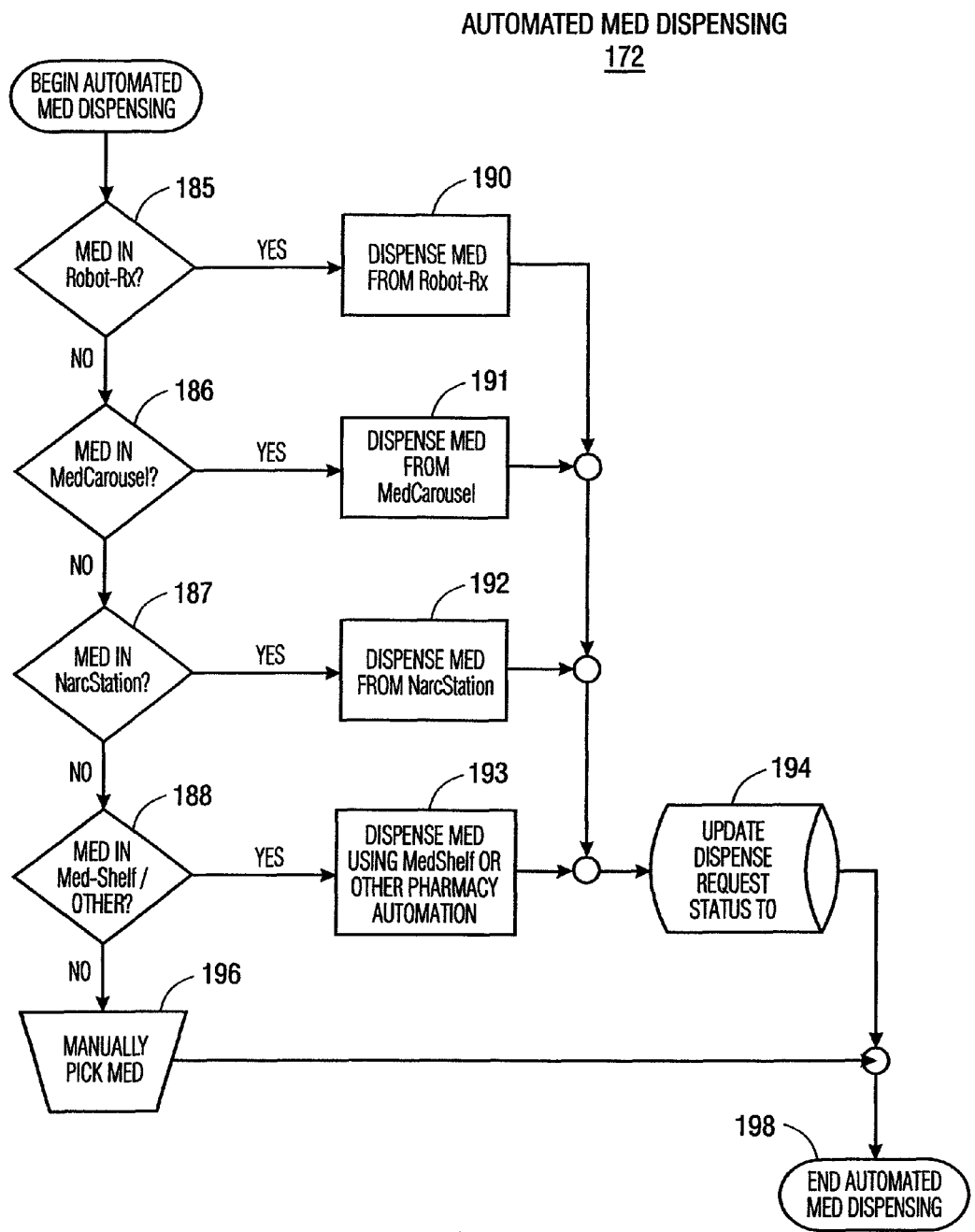

Returning to the inquiry 56, if Connect-Rn is enabled, then the user is given the option 72 of creating a dispense list. If a dispense list is to be created, the dispense list may be built according to the workflow illustrated in FIGS. 4A and 4B, represented by the box 74 in FIG. 3. Thereafter, or if the dispense list is not to be built, process flow continues with the inquiry 76. Inquiry 76 determines if any of the medications is missing. If medications are missing, a procedure for generating and processing a missing medication request may be performed as shown in FIGS. 5A-5C, represented by box 78 in FIG. 3. Thereafter, or if no medications are missing, process flow continues with process 58.

Process 58, as mentioned above, is implemented by the workflow illustrated in FIG. 6A-6F in which medications are collected and dispensed. An inquiry 80 is made to determine if it was possible to collect all of the medications. If all the medications were successfully collected, process flow continues with the inquiry 60. However, if all of the medications were not successfully collected, an inquiry 82 is made as to whether Connect-Rn is enabled. If yes, a request for missing medications can be performed as represented by the process 78. If not, medications need to be requested in another manner, such as calling the pharmacy. Thereafter, process flow continues with the inquiry 60.

FIGS. 4A and 4B illustrate a workflow for building a list of medications to dispense and a document dispense workflow, respectively. In FIG. 4A, the process begins at 90 in which medications and their locations are displayed. An exemplary screen shot is illustrated in FIG. 4C which illustrates one technique for displaying a medication together with its location. After the medications and their locations are displayed, an inquiry 92 determines if any medications have been previously dispensed but not yet administered. If answered in the affirmative, at 94 the drug and the person who dispensed the drug are illustrated. Thereafter, or if no medications were previously dispensed but not administered, process flow continues at 96. At 96, medications residing in a dispensing cabinet such as the AccuDose dispensing cabinet 22 may be selected. As seen from FIG. 4C, various medications are shown as being available in cabinet station: 1. Those medications may be selected to build a dispense list.

Thereafter, an inquiry 98, is made as to whether the selected medications should be saved as a dispense list. If the inquiry is answered in the affirmative, then the dispense list is saved at 100 to the central database (42 in FIG. 2) or, if answered in the negative, the dispense list is discarded at 102. From both 100 and 102, process flow continues at inquiry 104 which is an inquiry regarding whether to select non-due medications. If that determination is answered in the affirmative, a display of non-due medications is provided at 106. An exemplary display is illustrated in FIG. 4D. From 106, process flow continues with an inquiry 108 which determines whether to add the selections to the dispense list. If that inquiry is answered in the affirmative, the selections are added at 110 to the dispense list on the central database or, if answered in the negative, the selections listed are discarded at 112. From either 110 or 112, the dispense list created may be displayed at 114. An exemplary dispense list is illustrated is FIG. 4E. As seen from FIG. 4E, a variety of medications are available in patient specific cassettes, certain medications are available at a dispensing cabinet, while the location of other medications is unknown. After the list has been displayed, or from the "no" branch of inquiry 104, an inquiry 116 is made as to whether more medications are to be selected. If yes, process flow returns to 96. If no, process flow continues with the document dispense work flow illustrated in detail in FIG. 4B, represented by box 118 in FIG. 4A. Thereafter, the process terminates at 120.

Continuing with FIG. 4B, the process begins with an inquiry 124 in which a determination is made if Connect-Rn is enabled. If Connect-Rn is not enabled, then preparation of the dispense documents cannot be performed at this time and the process ends at 140. If Connect-Rn is enabled, process flow continues with inquiry 126 in which a determination is made as to whether the ordering physician is known. If the ordering physician is not known, the ordering physician is determined and entered at 128. Thereafter, or if the ordering physician was known, an inquiry 130 is made as to whether this is an override order. If it is determined that this is not an override order, then process flow terminates at 140. If this is an override order, then an inquiry 132 is made as to whether an override witness is required. If yes, the witness is recorded at 134. After the witness is recorded, or if no witness is necessary, an inquiry 136 is made as to whether an override reason is required. If an override reason is required, the override reason is entered at 138. Thereafter, or if no reason is required, process flow ends at 140. The reader desiring more information about override situations is directed to U.S. Pat. No. 6,650,964 entitled Medication Dispensing Apparatus Override Check And Communication System and U.S. Pat. No. 6,671,579 entitled Override Having Built In Audit Trail For Medication Dispensing And Administering Systems, both of which are hereby incorporated by reference in their entireties.

Returning briefly to FIG. 3, process 74 builds the dispense list as described in conjunction with the workflows of FIGS. 4A and 4B. After the dispense list is built, the inquiry 76 determines whether any of the medications are missing. If medications are missing, the request for a missing medication can be made and that request filled as will now be described in conjunction with FIGS. 5A-5C. In FIG. 5A, an inquiry 144 is made whether the ordered medication for a patient is found in the unit. If it is, process flow continues with inquiry 146 which determines whether additional medications are to be found. If not, the process ends at 148. If more medications are to be found, process flow continues by returning to inquiry 144.

At inquiry 144, if it is determined that the ordered medications are not found in the unit, another inquiry 150 determines whether Connect-Rn is enabled. If Connect-Rn is enabled, then the drug and quantity may be selected at 152. An exemplary screen shot 153, connected to 152 via a broken line, illustrates the information which may be displayed and from which a selection can be made. After a selection is made, the selected drug and quantity is stored as a missing medication request in central database (42 in FIG. 2) at 154. Thereafter, the missing medication request is processed as will be described in conjunction with the process 156 illustrated in detail in FIG. 5B. The status of the processing of the missing medication request may be displayed at 158. The display may include an estimated time of arrival. From either 158, or 150 if that inquiry results in a negative determination, process flow continues with inquiry 146.

Turning to FIG. 5B, the missing medication request is stored in the central database at 160. Inquiry 162 determines, based on user preferences, available hardware, among others, whether the request should be sent to a printer, some type of pharmacy software, or delivered directly to automation equipment for filling the missing medication request. The phrase Automation equipment refers to automated (e.g. Robot-Rx robot) or semi-automated (e.g. MedCarousel, NarcStation) hardware used for filling a prescription. In the case of delivery of the missing medication request to a printer, a missing medication request is printed at 164. Printing typically indicates that the request is to be filled in a manner that does not rely upon automation equipment for filing the prescription. In the case of delivering the missing medication request to some type of pharmacy system, that may be accomplished by sending the missing medication request to a MedDirect device. A missing medication icon and information are generated and placed into a missing medication folder at 166. An alert condition is created at 168. From either 164 or 168, an inquiry 170 is made if the request may be forwarded to automation equipment or if a manual pick of the medication is required. If the request may be forwarded onto automation equipment, or directly from inquiry 162, the request is forwarded to automation equipment which executes a workflow as shown, for example, in FIG. 5C, represented by box 172 in FIG. 5B. After the medication has been dispensed at 172, the medication is then delivered to the floor at step 174, using any appropriate delivery system, e.g. runner, tube system, cart/cassette from a robot, etc. The incident is archived at 176 and the process ends at 178.

Returning to inquiry 170, if it is determined that the request may not be forwarded to automation equipment, a manual pick is performed at 180. After the manual pick is performed at 180, an inquiry 182 is made to determine if the request came from a pharmacy system. If the answer is yes, then the status of the missing medication is updated at 184 in the pharmacy system. For example, the pharmacy system may be notified that the prescription has been filled so its status can be changed to delivered. Thereafter, or if the request did not come from a pharmacy system, process flow continues at 174 with the medication being delivered to the floor in any suitable manner.

In FIG. 5C, dispensing of the missing medication through the use of automation equipment is illustrated. A series of inquiries 185-188 determines the equipment in which the missing medication may be found. More specifically, inquiries are made as to whether the medication is in a robot 185, in a carousel 186, in a NarcStation 187 or in a med shelf or other device 188. If any of those inquiries is answered in the affirmative, then a dispense is performed from the appropriate device. For example, if the medication is determined at 185 to be in the robot, a dispense from the robot is performed at 190. If the medication is determined to be in a carousel at 186, a dispense from the carousel is performed at 191. If a determination is made at 187 that the medication is in a NarcStation, a dispense from the NarcStation occurs at 192. If it is determined at 188 that the medication is in a shelf or other location, a dispense from the shelf or other pharmacy automation occurs at 193. After the dispense 190-193, the status of the missing med request is updated at 194. The update 194 may be similar to or the same as the update 184 in FIG. 5B. The process ends at 198. If it is determined after all of the inquiries 185-188 that the medication is not in automation equipment, then the medication is manually picked at 196 and the process ends at 198.

Additionally, instead of being determined serially as shown in FIG. 5C, followed by a filling process, a determination may first be made as to which automation equipment contains the medication, and then logic may be used to determine which automation equipment is best suited to fill the request, e.g. fill the prescription with the device having the oldest stock, the device having the least amount of stock, etc.

Although not shown in FIGS. 5A-5C, it is possible the missing medication request may be denied for a variety of reasons, e.g. out of stock, medication not approved for patient, etc. Under such circumstances, a message may be sent to the user indicating that the request has been denied or cannot be fulfilled.

Not shown in FIGS. 5A-5C are additional inquiries that may be incorporated into the workflow. For example, an inquiry can be made to determine if the requested missing medication is in the next cart fill. If yes, an inquiry can be made to determine if the cart fill delivery will be timely. If delivery is timely, the missing medication request need not be filled again. If the medication is not in a cart being delivered, or if it is in a cart being delivered, but delivery will not be timely, an inquiry can be made to determine if a cabinet refill is pending. If yes, and the refill is timely, it is not necessary to fill the missing medication request.

Figure 6A:
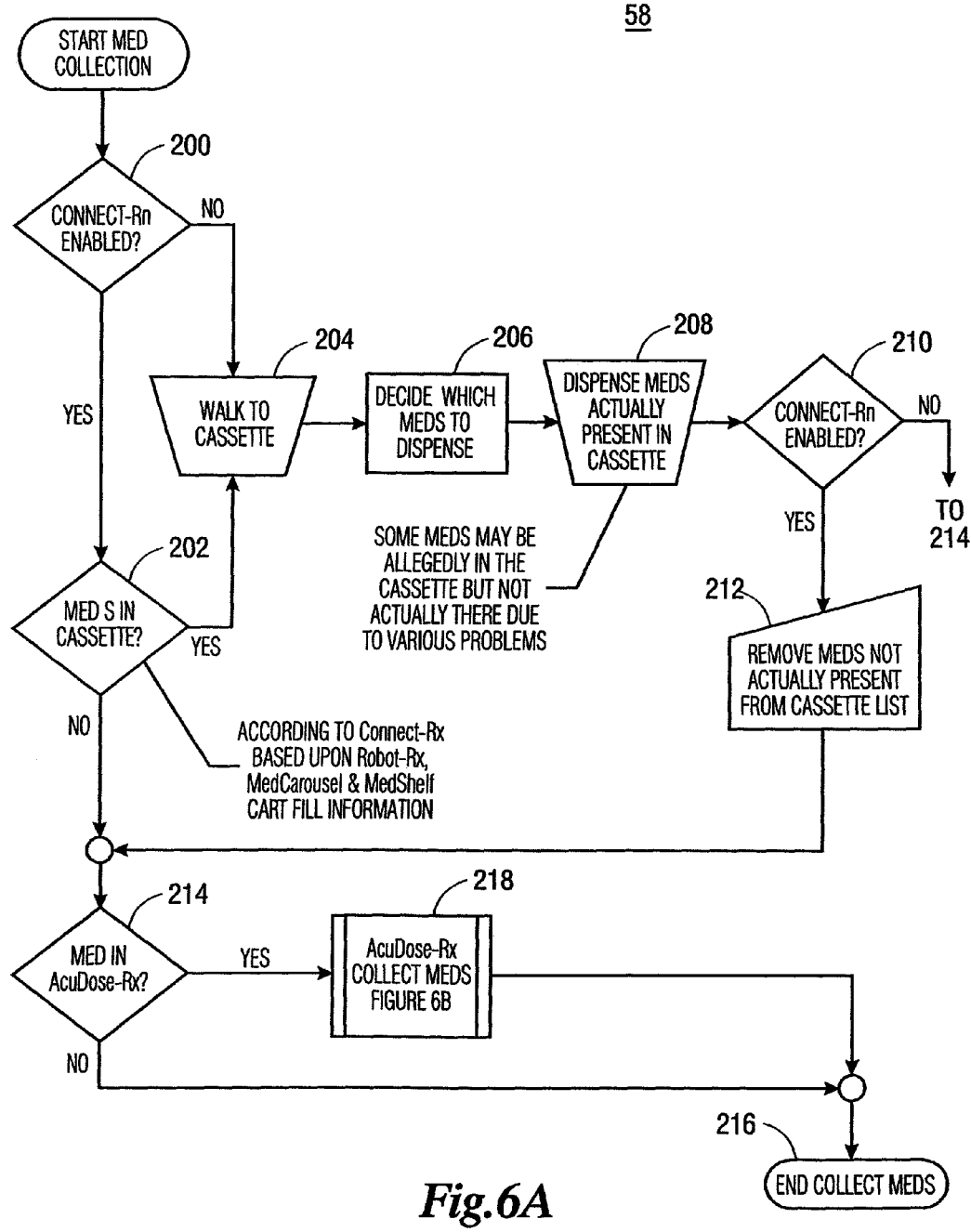
FIGS. 6A-6F illustrate a workflow for collecting and dispensing medications.

In FIG. 6A, an exemplary workflow 232 for collecting and dispensing of medications is illustrated. The workflow 232 of FIG. 6A begins at inquiry 200 in which a determination is made as to whether Connect-Rn is enabled. If it is enabled, another determination is made at inquiry 202 as to whether the medications are identified as being in a cassette. If that inquiry is answered in the affirmative, or if it is determined at inquiry 200 that Connect-Rn is not enabled, the user needs to walk to the cassette as illustrated by 204. At 206 the user determines which medications to dispense from the cassette. At 208 medications which are to be dispensed, and which are actually present in the cassette, are dispensed. It should be noted that some medications may be identified at 202 as being in the cassette, but not actually in the cassette due to various problems.

After the medications are dispensed at 208, inquiry 210 determines if Connect-Rn is enabled. If Connect-Rn is enabled, then the list of medications is updated at 212 to remove any medications on the list (indicating that they are present in the cassette), but not actually present in the cassette, and to decrement the count for medications that have been removed. Thereafter, process flow continues with inquiry 214. If, at 210, Connect-Rn is not disabled, process flow continues with inquiry 214.

At inquiry 214, a determination is made whether the medications are in a dispensing cabinet, such as the AccuDose-Rx cabinet. If not, the collection of medication ends at 216. If, however, the inquiry at 214 is in the affirmative, then a procedure 218 for collecting medications from the cabinet is performed, as shown in greater detail in FIG. 6B. Thereafter, the process ends at 216.

Figure 6B:
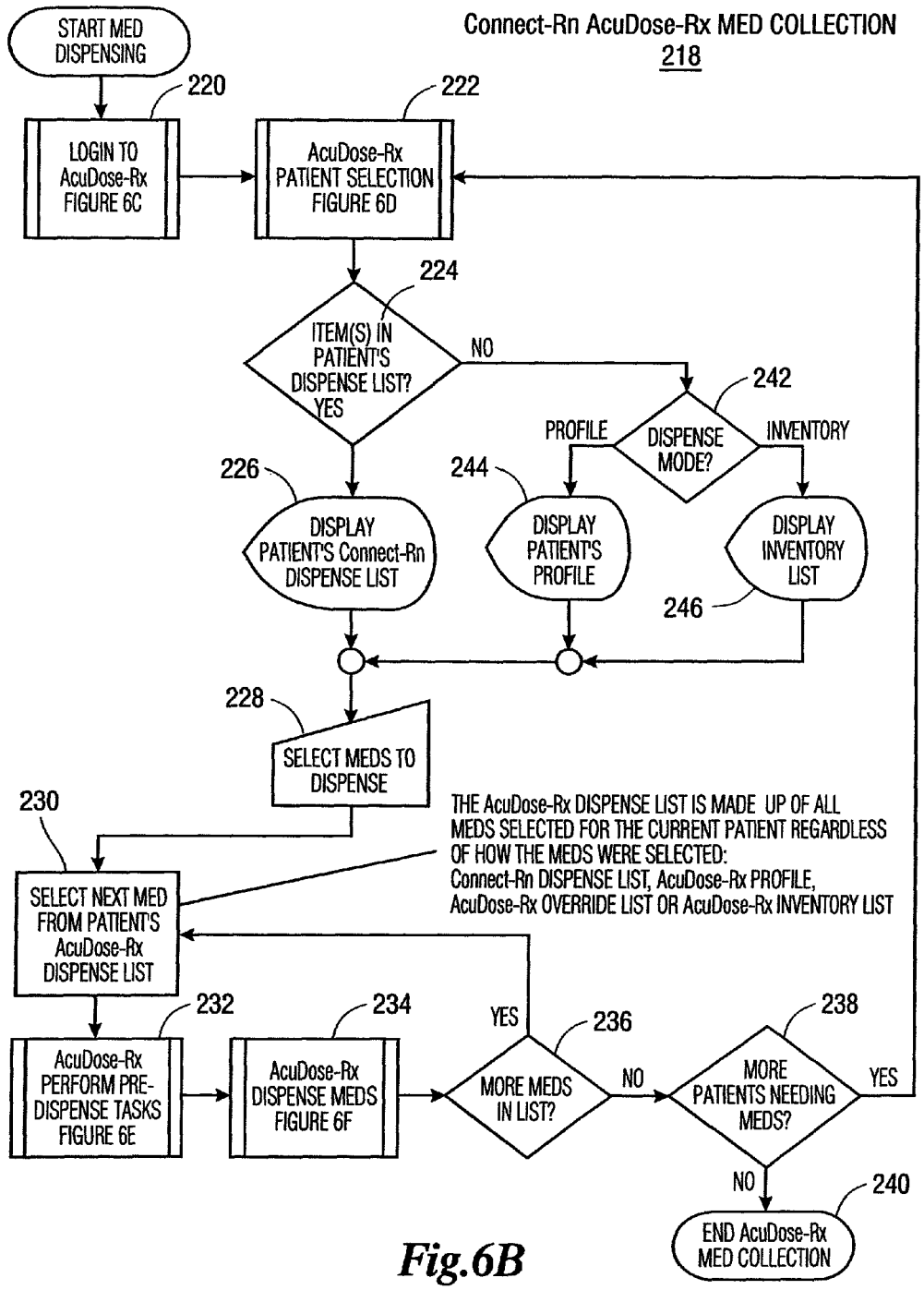

FIG. 6B illustrates an exemplary workflow 218 for collecting medications from an automated cabinet such as the AccuDose-Rx cabinet. The process begins with a login procedure 220 to the cabinet. The login procedure 220 is shown in greater detail in FIG. 6C. After the login procedure 220, a patient is selected by a process 222 discussed in greater detail hereinbelow in conjunction with FIG. 6D. After a patient has been selected by process 222, a determination is made at inquiry 224 if there are items in that patient's dispense list. If that determination is answered in the affirmative, then the selected patient's dispensed list is displayed at 226. Thereafter, at 228, medications are selected to be dispensed. The dispense list for an AccuDose-Rx cabinet is made up of all medications selected for the current patient regardless of how the medications were selected, e.g. from a Connect-Rn dispense list, an AccuDose-Rx profile, an AccuDose-Rx override list, an AccuDose-Rx inventory list, among others.

The dispensing cabinet may then perform pre-dispense tasks as represented by the box 232 and as described in greater detail in conjunction with FIG. 6E hereinbelow. The medications are dispensed according to a process 234 discussed in greater detail in conjunction with FIG. 6F. After dispensing of the medications, an inquiry 236 determines if there are more medications on the dispense list. If yes, process flow returns to 230. If not, an inquiry 238 determines if there are more patients for which medications are to be dispensed. If yes, process flow returns to process 222. If not, the process ends at 240.

Returning to the inquiry 224 as to whether there were any items in the patient's dispense list, if that determination is negative, a subsequent inquiry 242 determines the dispense mode. There are numerous possible dispense modes. In the exemplary workflow illustrated in 6B, two dispense modes, dispense by profile and dispensed by inventory, are possible. If there is to be a dispense by profile, then the patient's profile is displayed at 244. If there is to be a dispense by inventory, then the inventory list is displayed at 246. From either 244 or 246, process flow continues with 228 in which medications are selected to dispense.

Figure 6C:
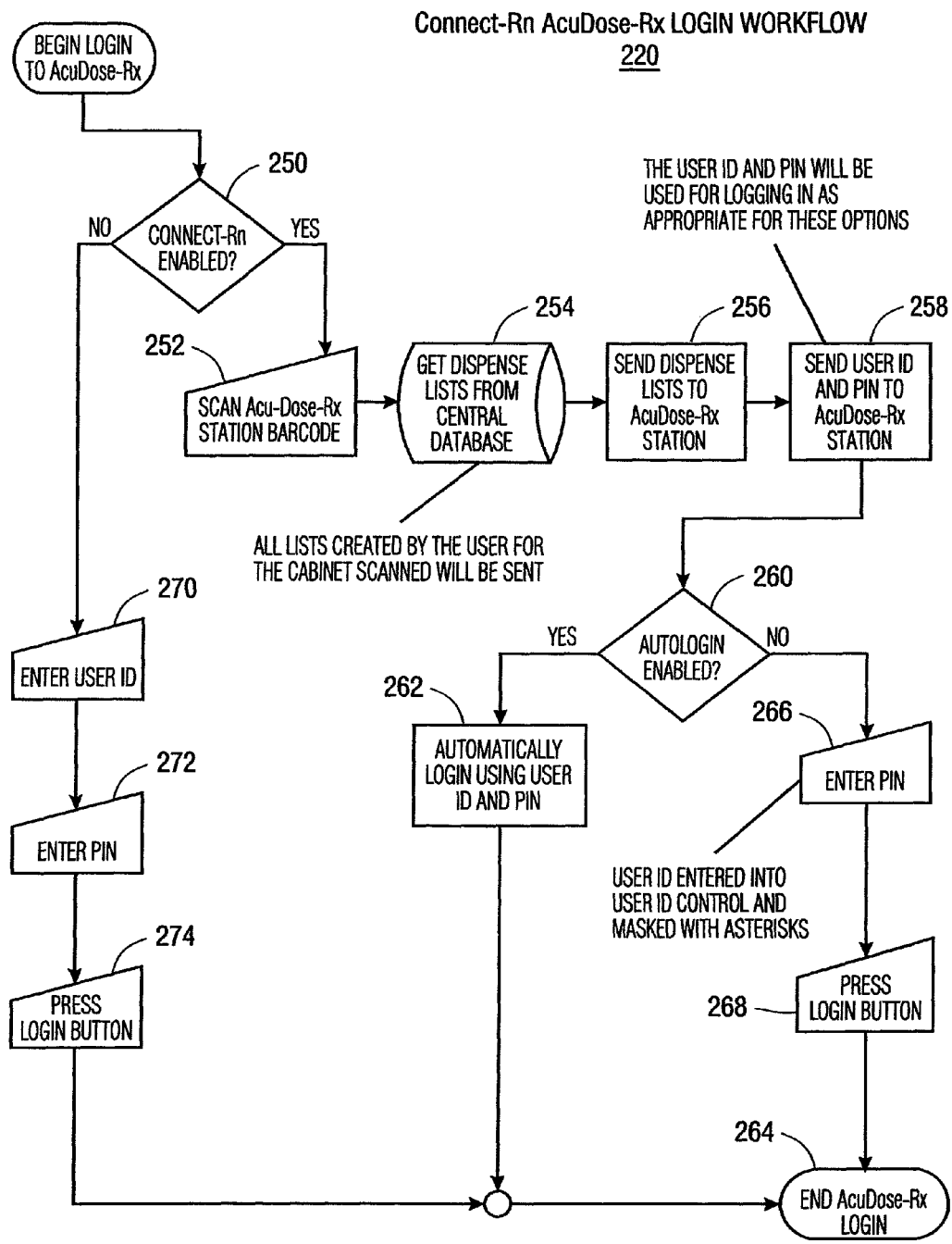

Turning to FIG. 6C, an exemplary login process 220 is illustrated. An inquiry 250 determines whether Connect-Rn is enabled. If yes, the user uses an authentication device to confirm that the user is located proximate to the cabinet. The authentication device may take the form of a bar code which is scanned at 252. Other types of authenticating devices may be used such as an RF ID tag embedded in the badge of the user, a fingerprint scanning device, or other biometric device, among others.

After the user confirms that the user is located proximate to the dispensing device, the dispense lists are located on the central server at 254. All lists created by the user for this cabinet will be transferred at 256. The user's ID and PIN number are transferred at 258. The transfer is preferably a wireless RF transmission, but could be by other means, e.g. physical docking of the hand held device 10 with a docking station (not shown).

At inquiry 260 a determination is made as to whether an autologin is enabled. If yes, the user is automatically logged in using the user ID and PIN number transferred to the cabinet. It will be seen from the foregoing that if Connect-Rn is found to be enabled at inquiry 250, and the autologin found to be enabled at inquiry 260, the user's logon to the cabinet is seamless and transparent to the user. The user simply scans the bar code at 252, or operates some other type of authentication device for confirming that the user is at the cabinet, and the user is automatically logged in. Thereafter, the login process ends at 264.

If, at inquiry 260, the autologin is not enabled, the user must enter their PIN at 266 and press a login button, or take some other confirmatory action, at 268. The process ends at 264.

Returning to the inquiry 250, if Connect-Rn is not enabled, the user must manually login by entering the user's ID at 270, entering the user's PIN at 272, and pressing a login button at 274, or taking some other confirmatory action. The login process ends at 264.

Figure 6D:
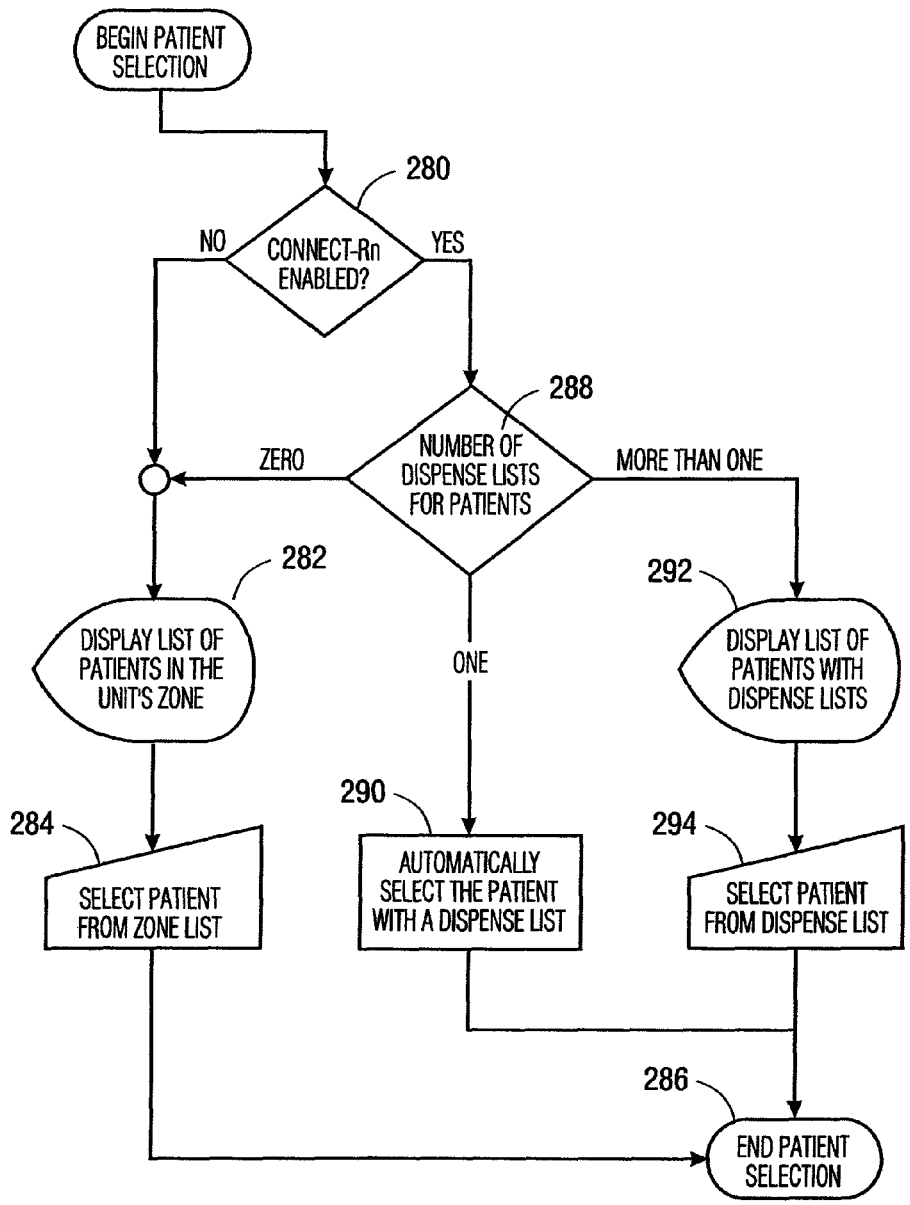

FIG. 6D illustrates an exemplary workflow 222 for selecting a patient. At inquiry 280, a determination is made as to whether Connect-Rn is enabled. If Connect-Rn is not enabled, a list of patients is displayed at 282. For example, all patients in the user's, unit's zone may be displayed. At 284 a patient is selected from the list, e.g. the zone list, among others. The process ends at 286.

Returning to the inquiry 280, if Connect-Rn is enabled, a determination is made regarding the number of patients for which dispense lists have been created. If the number is zero, the process continues at 282 by displaying a list of all the available patients. If only one patient has a list, that patient is automatically selected at 290 and the process terminates at 286. If there is more than one patient with a list, the list of patients with dispense lists is displayed at 292. At 294 the user selects a patient from the dispense list and the process ends at 286.

Figure 6E:
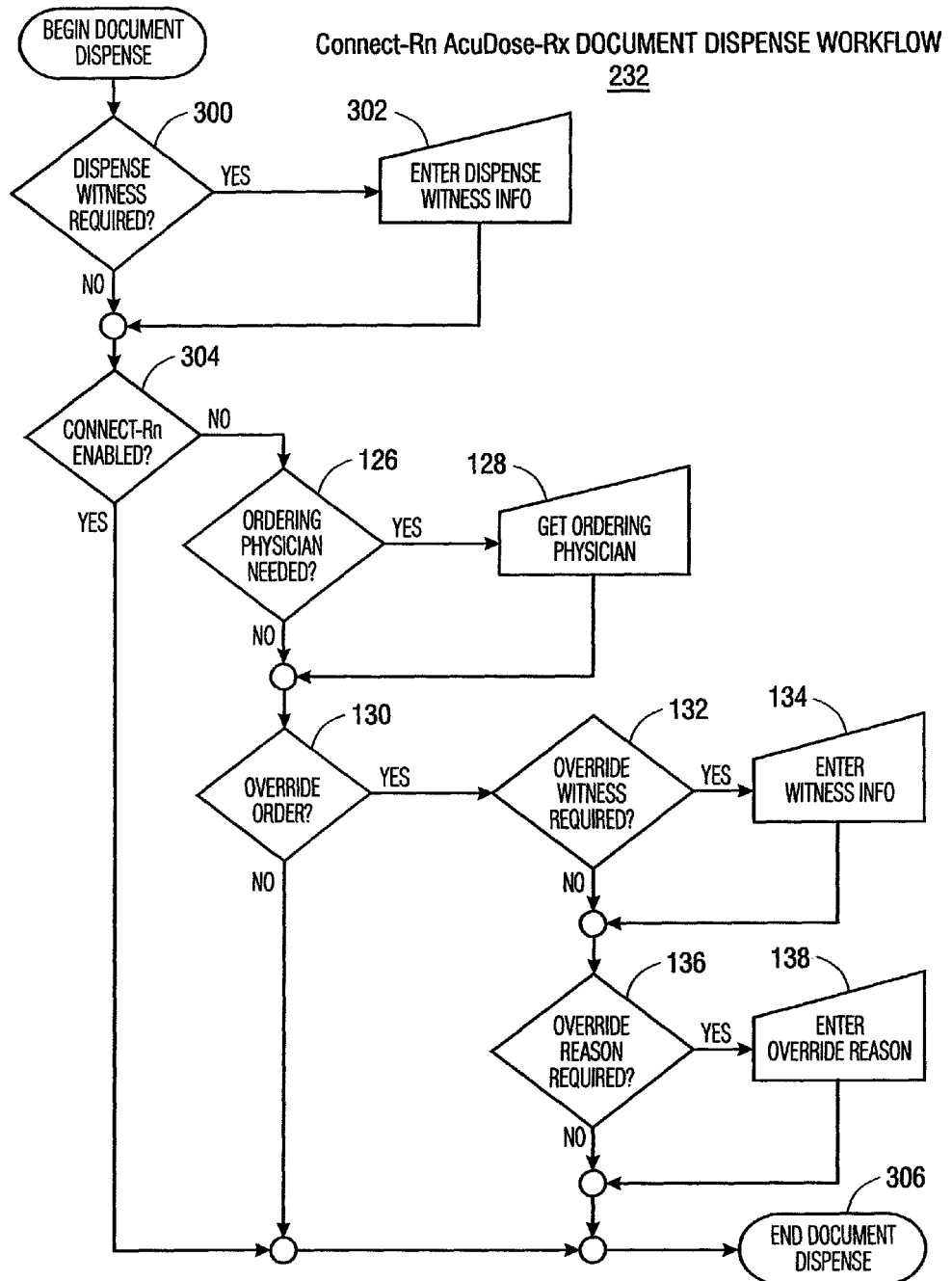

In FIG. 6E, an exemplary workflow 232 for the document dispense process is illustrated. Beginning at inquiry 300 a determination is made if a dispense witness is required. If a dispense witness is required, the dispense witness information is entered at 302. Thereafter, or if no dispense witness is required, a determination is made at 304 if Connect-Rn is enabled. If yes, then the document dispense workflow has already been completed as discussed in conjunction with FIG. 4B and the process ends at 306. If Connect-Rn is not enabled, then the various inquiries, i.e. is the ordering physician needed 126, is this an override order 130, etc. are made as discussed above in conjunction with FIG. 4B. When completed, the process ends at 306.

Figure 6F:
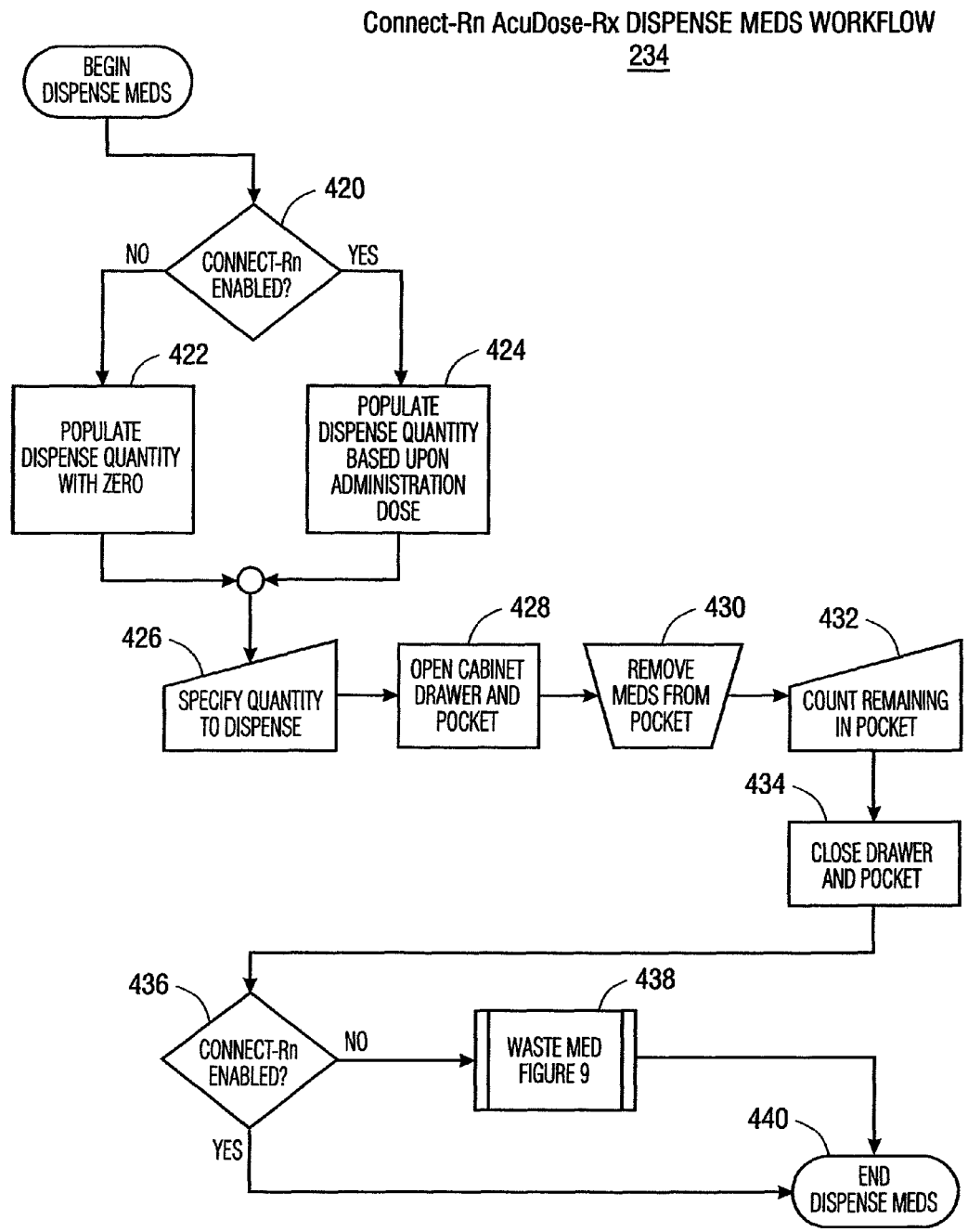

The process 234 for dispensing medications is illustrated in FIG. 6F. The process for dispensing medications 234 begins with an inquiry regarding whether Connect-Rn is enabled. If not, the dispense quantity is automatically populated with zero at 422, and if enabled, the dispense quantity is automatically populated based upon the administration dose at 424. From either 422 or 424, the user specifies or adjusts the quantity to dispense at 426. The cabinet drawer and pocket are opened at 428. At 430 the medications are removed from the pocket and a count is made of the medications remaining in the pocket at 432. The count may be used to update inventory records. The pocket and drawer are then closed at 434.

An inquiry 436 determines whether Connect-Rn is enabled. If not, a waste medication process 438 can be performed as discussed in detail in conjunction with FIG. 9. If Connect-Rn is not enabled, or after the waste medication process 438 is performed, the process ends at 440.

Returning briefly to FIG. 3, it is seen that process 64 is a process for issuing supplies, which is described in detail in conjunction with FIG. 7. It should be noted, however, that the workflow for issuing supplies 64 need not be performed in the sequence illustrated in FIG. 3. For example, the issue supplies procedure 64 could be performed before the collection of medications procedure 58 or may be performed after the medications have been administered according to the process 68. Furthermore, the issue supplies procedure 64 could be performed in a manner such that supplies are issued prior to the dispensing of medications. Thus, the issue supplies procedure 64 may be viewed as a stand alone procedure, the performance of which is unrelated to the creation of the list of medications to be dispensed, location of the medications to be dispensed, collection of the medications to be administered as well as the administration of the medications.

Figure 7A:
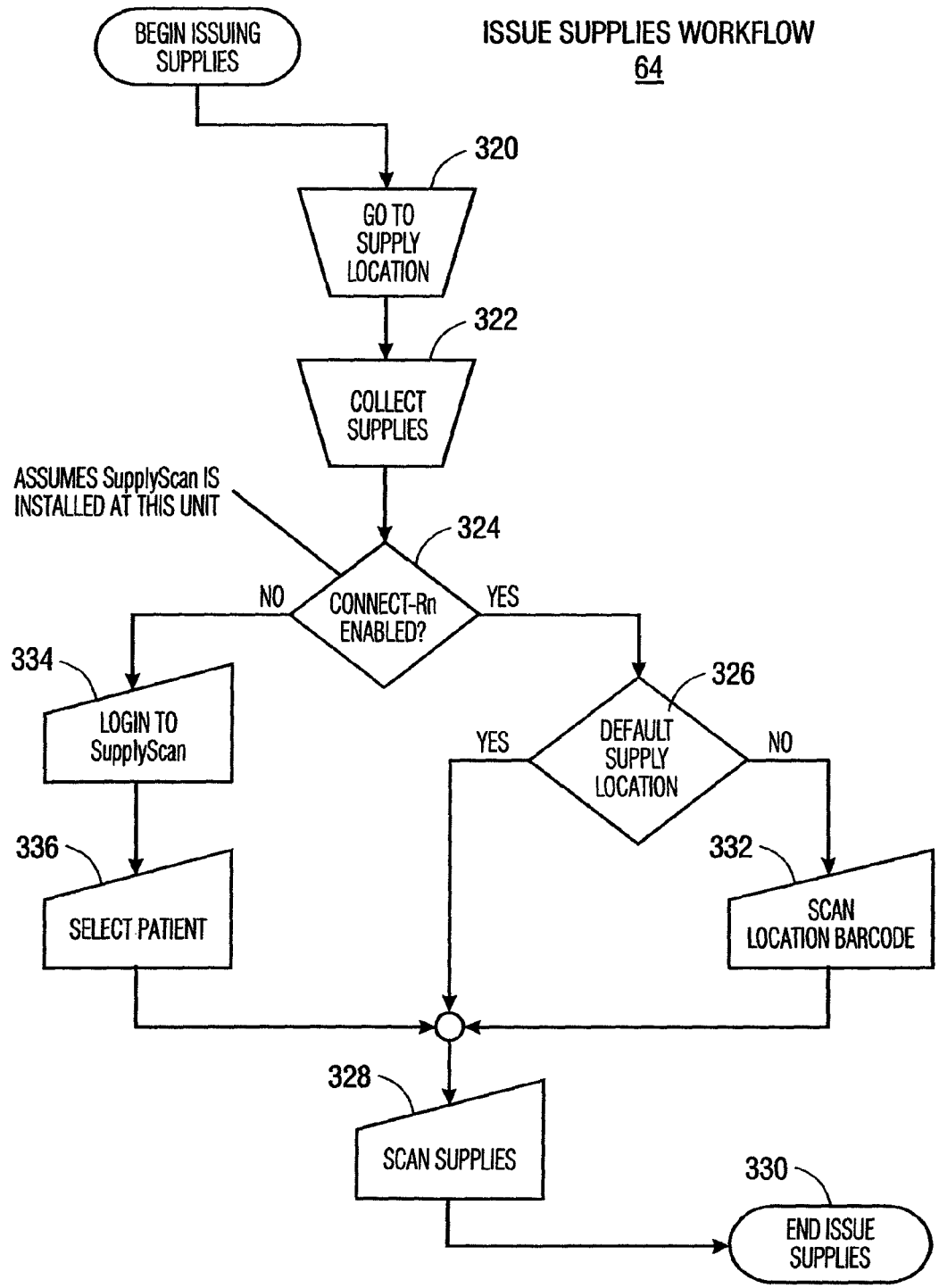
FIG. 7 illustrates a workflow for issuing supplies.
Figure 8:
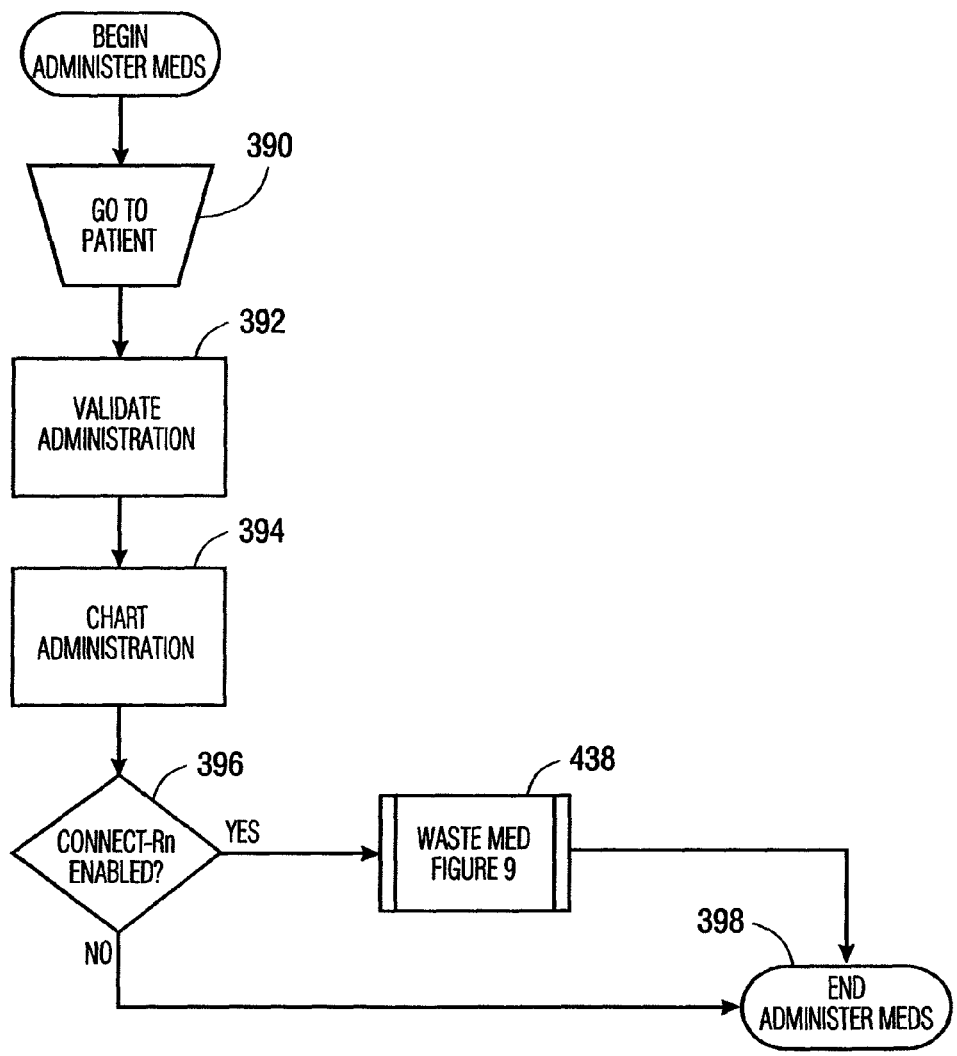
FIG. 8 illustrates a workflow for administering medications and issuing supplies.

FIG. 7A illustrates an exemplary workflow 64 for issuing supplies. The workflow begins when the user goes to a supply location as represented by 320. Thereafter, supplies are collected at 322. At inquiry 324 a determination is made if Connect-Rn is enabled. If yes, at inquiry 326 a determination is made if the user is at the default supply location. If the user is at the default supply location, then the supplies are scanned at 328 and the process ends at 330. Alternatively, if the user is not at the default supply location, then the supply location is entered at 332 and process flow continues with the scanning of the supplies at 328. The supply location may be entered in a variety of ways such as scanning a bar code, automatically reading an RF ID tag, among others.

If, at inquiry 324, it is determined that Connect-Rn is not enabled, the user will be required to login to a supply issuing system, such as the Supply Scan system available from McKesson. After logging on through the supply issuing system's computer (See 20, FIG. 1), a patient is selected at 336 and the supply scanned at 328. The process can be repeated for additional patients.

Figure 7B:
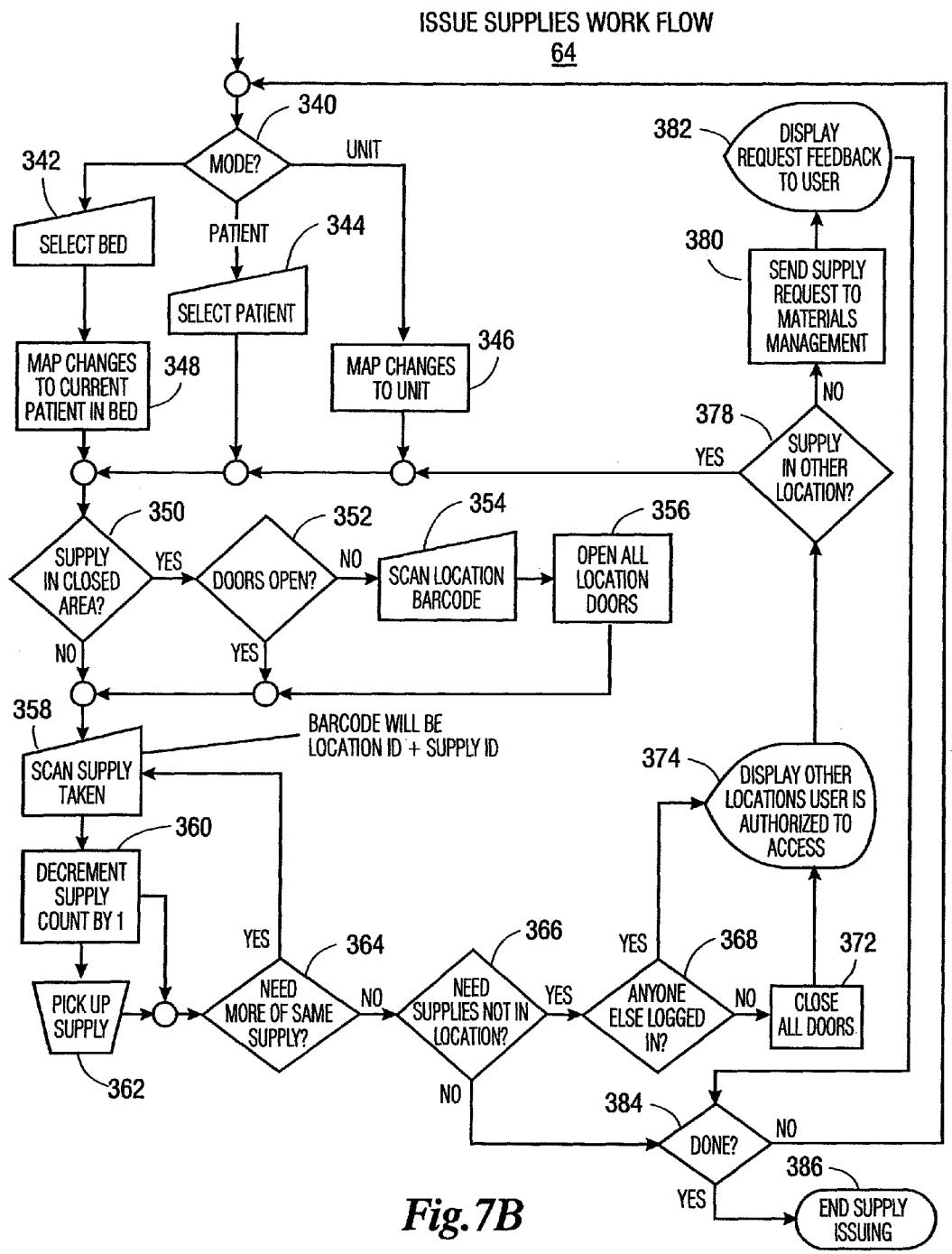

Another process for issuing supplies is illustrated in FIG. 7B. The process illustrated in FIG. 7B assumes that Connect-Rn is available. After the user has gone to a supply location, the process begins at inquiry 340 where a determination is made as to the issuing mode. The issuing mode may be select by bed 342, patient 344, or by mapping charges to a unit 346. If the select bed 342 mode is chosen, charges are mapped at 348 to the current patient in the selected bed. From either 348, 344 or 346 process flow continues with an inquiry 350 to determine if the supply is in a closed area. If yes, inquiry 352 determines if the doors are open. If they are not, the location bar code is scanned at 354 and all location doors are open at 356. After the doors are open at 356, or it is determined at 352 that the doors are already open, or if the supply is not in a closed area, process flow continues at 358. At 358 the supply is scanned. At 360, the supply count is decremented by one and the user picks up the supply at 362. Inquiry 364 determines if more of the same supply is needed. If yes, process flow returns to 358. If not, process flow continues with inquiry 366 which determines if supplies are needed which are not in this location. If the answer is yes, an inquiry 368 determines if anyone else is logged in and, if not, all doors are closed at 372. After the doors are closed at 372, or if it is determined that others are logged in at 368, other locations the user is authorized to access are displayed at 374. An inquiry 378 determines if the supply is in one of these other locations. If yes, process flow continues with the inquiry 350. If no, process flow continues with 380 in which a supply request is sent to materials management. Feedback is displayed to the user at 382 and process flow continues with enquiry 384 which determines if the user is done issuing supplies. If yes, the procedure ends at 386 and, if not, the procedure continues by returning to inquiry 340.

Returning to the inquiry 366, if it is determined that the user does not need supplies in another location, process flow may continue with the inquiry 384. If desired, the determination as to whether anyone else is logged in and, if not, closing all the doors may be performed between the inquiry 366 and the inquiry 384.

Returning briefly to FIG. 3, the process 68 for administration of medications and supplies is shown in greater detail in FIG. 8. FIG. 8 begins with the user going to the patient at 390. The administration is validated at 392 using procedures appropriate to that healthcare institution. Thereafter, the administration is charted at 394.

At inquiry 396, a determination is made as to whether Connect-Rn is enabled. If not, process flow ends at 398. If Connect-Rn is enabled, process flow continues with the waste medication procedure 438 shown in detail in FIG. 9. Process flow ends at 398.

Figure 9:
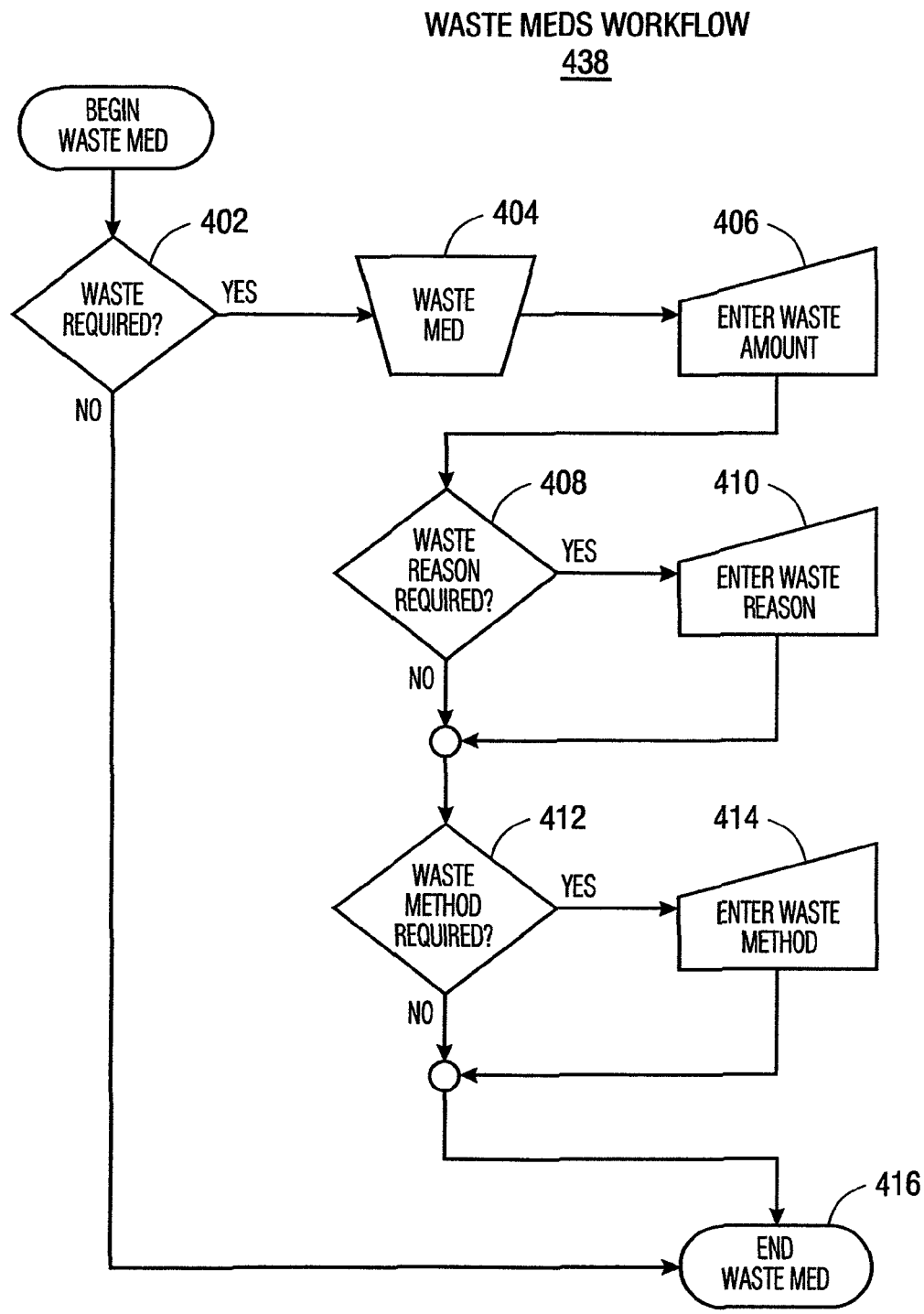
FIG. 9 illustrates a workflow for handling waste medications.

The workflow for the waste medication procedure 438 illustrated in FIG. 9 begins with an inquiry 402 to determine if a medication is to be wasted. A waste situation can arise due to a number of different factors. For example, a patient may be prescribed a 250 milligram dose, but the medication is provided in a 500 milligram tablet. Under such circumstances, the tablet is broken in half, with one half being administered to the patient and the other half wasted. Should such a situation occur, the medication is wasted at step 404 according to whatever procedures may be applicable for that medication. At 406 the waste amount is entered.

At inquiry 408, a determination is made as to whether a reason for the waste is required. If yes, the reason for the waste is entered at 410. Thereafter, or if no waste reason is required, process flow continues with inquiry 412 in which a determination is made as to whether the waste method must be documented. If yes, the waste method is documented at 414. Thereafter, or if no waste method documentation is required, the process ends at 416.

Returning to FIG. 3, process 58 is for collecting and dispensing medications as discussed more fully in conjunction with FIG. 6A. In FIG. 6A, it is assumed that the nurse or healthcare worker is gathering medications and placing the medications in their pocket or perhaps into some type of container. The present invention contemplates the use of a mobile cart. In the event that a mobile cart is available to the nurse or healthcare worker the workflow of FIG. 10 may be implemented in place of the workflow of FIG. 6A.

In FIG. 10, the workflow begins at 450 by moving the cart to the patient specific cassettes. An inquiry 452 determines whether any of the cassettes are for patients for which the nurse is to administer medications. If that inquiry is answered in the affirmative, the nurse scans the cassette bar code 454 and scans all medications in the patient specific cassette at 456. By scanning all the medications in the patient specific cassette, the nurse is counting the number of doses of each medication and associating those doses with the patient. When the scanning is done, the quantity of medications in each cassette will be accurately documented. The cassette is then loaded into the cart at 458 and workflow returns to the inquiry 452 to determine if there are any additional cassettes for this nurse. If not, process flow continues with 460 where the cart is locked. An inquiry is made at 462 to determine if Connect-Rn is enabled. If not, the nurse proceeds to the cabinet as shown by 464. If Connect-Rn is enabled, a determination is made at 466 if medications are in a dispensing cabinet. If yes, the nurse proceeds to the cabinet and either from inquiry 466 or step 464, the nurse unlocks the cart at 468. The nurse then performs the process 218 of collecting medications which has previously been described in connection with FIG. 6B. After the process 218 of FIG. 6B is completed an inquiry is made at 470 to determine if there are medications to load. If the nurse went directly to the cabinet without Connect-Rn being enabled, it is possible that there were no medications in the cabinet to be dispensed and thus the determination 470 is needed. If medications have been dispensed as a result of process 218, the nurse scans the cassette at 472 and then loads the medication into the cassette at 474. Medication quantities dispensed as a result of process 218 are thus automatically added to the cassette's medication counts. After all the medications have been loaded, or if no medications were in the cabinet as determined by inquiry 466, the cart is locked at 476 and the workflow for collecting medications ends.

It should be noted that patient cassettes typically contain a day's worth of medications for a patient while dispenses from a cabinet are usually the next due medications. Thus, the dispense from the cabinet may need to be adjusted if the healthcare worker wishes to have a full day's worth of medications for patient's on that healthcare worker's rounds.

The present invention provides additional functionality for nurses as set forth in the figures. The present invention also adds greater value to the wireless infrastructure investment. By integrating the functionality set forth in FIG. 1 in a handheld device 10, mobile cart, or other portable device, an integrated suite of tools can be provided which allows the nurse to perform his or her duties in a seamless manner regardless of the duty or location in which it is performed. For example, new prescriptions and new orders may be scanned and input to a pharmacy system as soon as they are written by a physician. Nursing time is saved in that nurses can either obtain all their medications in one place or be directed to where the medications needed for a particular patient are located. With certainty in obtaining the medications at the indicated locations, it is less likely that nurses will "borrow" medications from other patient cassettes. A nurse can "prepick" patients and medications on the handheld device 10 so that time spent at a dispensing cabinet can be spent dispensing medications, rather than picking patients and medications. Additionally, the nurse can take the same handheld device 10 into a storage area and select medical supplies for a patient. Thereafter, the same handheld device 10 can be taken to a patient's bedside for administration of the dispensed medications and supplies.

That which is claimed is:

1. A method, comprising:
   receiving logon information into a system via a remote computer;
   receiving via the remote computer a list of medications to dispense, the list created by a user and containing different medications;
   confirming that the user is located proximate to a dispensing device; and
   transmitting the list of medications to the dispensing device upon confirming that the user is located proximate to the dispensing device.

2. The method of claim 1, additionally comprising administering medications using the remote computer.

3. The method of claim 1, wherein the list is organized per user and per patient.

4. The method of claim 1, wherein the dispensing device receives the logon information as logon information for the dispensing device.

5. The method of claim 1, additionally comprising identifying a location of medications to be dispensed within a medication dispensing system.

6. The method of claim 1, additionally comprising requesting from a pharmacy a medication which is missing from the dispensing system.

7. The method of claim 1, additionally comprising issuing supplies using the remote computer.

8. A method comprising:
   receiving logon information into a system via a remote computer;
   maintaining in a database an inventory of items located within a dispensing device;
   communicating with the database via the remote computer;
   receiving a list of medications to be dispensed, the list created by a user and comprising different medications;
   confirming that the user is located proximate to the dispensing device; and
   transmitting the list of medications to the dispensing device upon confirming that the user is located proximate to the dispensing device.

9. The method of claim 8, additionally comprising administering medications using the remote computer.

10. The method of claim 8, wherein the list is organized per user and per patient.

11. The method of claim 8, wherein the dispensing device receives the logon information as logon information for the dispensing device.

12. The method of claim 8, additionally comprising identifying a location of medications to be dispensed within a medication dispensing system.

13. The method of claim 12, additionally comprising requesting from a pharmacy a medication which is missing from the dispensing system.

14. The method of claim 8, additionally comprising issuing supplies using the remote computer.

15. The method of claim 8, additionally comprising updating the inventory of items located within the dispensing device.

16. A method, comprising:
    receiving logon information into a system via a remote computer;
    maintaining in a database an inventory of items located within a dispensing system;
    communicating with the database via the remote computer to identify a location within the medication dispensing system where a medication to be dispensed is located;
    receiving a list of medications to dispense, the list created by a user and comprising different medications;
    confirming that the user is located proximate to a dispensing device; and
    transmitting the list of medications to the dispensing device upon confirming that the user is located proximate to the dispensing device.

17. The method of claim 16, additionally comprising administering medications using the remote computer.

18. The method of claim 16, wherein the list is organized per user and per patient.

19. The method of claim 16, wherein the dispensing device accepts the logon information input to the system as logon information for the dispensing device.

20. The method of claim 16, additionally comprising requesting from a pharmacy a medication which is missing from the dispensing system.

* * * * *

UNITED STATES PATENT AND TRADEMARK OFFICE
CERTIFICATE OF CORRECTION

PATENT NO.         : 8,170,714 B2
APPLICATION NO.    : 12/958065
DATED              : May 1, 2012
INVENTOR(S)        : Spano, Jr. et al.

Page 1 of 1

It is certified that error appears in the above-identified patent and that said Letters Patent is hereby corrected as shown below:

Column 1
Line 33, "create a bather" should read --create a barrier--.

Signed and Sealed this
Fifth Day of March, 2013

Teresa Stanek Rea
*Acting Director of the United States Patent and Trademark Office*